(12) United States Patent
Blanchard et al.

(10) Patent No.: US 9,501,822 B2
(45) Date of Patent: Nov. 22, 2016

(54) COMPUTER-IMPLEMENTED PLATFORM FOR AUTOMATED FLUORESCENCE IMAGING AND KINETIC ANALYSIS

(75) Inventors: Scott Blanchard, New York, NY (US); Daniel Terry, New York, NY (US); (Continued)

(73) Assignee: CORNELL UNIVERSITY, Ithaca, NY (US)

(*) Notice: Subject to any disclaimer, the term of this patent is extended or adjusted under 35 U.S.C. 154(b) by 326 days.

(21) Appl. No.: 13/982,401

(22) PCT Filed: Jan. 27, 2012

(86) PCT No.: PCT/US2012/022875
§ 371 (c)(1),
(2), (4) Date: Jul. 29, 2013

(87) PCT Pub. No.: WO2012/103423
PCT Pub. Date: Aug. 2, 2012

(65) Prior Publication Data
US 2013/0308842 A1    Nov. 21, 2013

Related U.S. Application Data

(60) Provisional application No. 61/437,203, filed on Jan. 28, 2011.

(51) Int. Cl.
*G06K 9/00* (2006.01)
*G06T 7/00* (2006.01)
*G01N 21/64* (2006.01)

(52) U.S. Cl.
CPC ......... *G06T 7/0012* (2013.01); *G01N 21/6408* (2013.01); *G01N 21/6456* (2013.01); *G01N 2021/6441* (2013.01)

(58) Field of Classification Search
None
See application file for complete search history.

(56) References Cited

U.S. PATENT DOCUMENTS 6,456,734 B1 * 9/2002 Youvan ............... G01N 21/278
                                                           382/100
7,298,476 B2   11/2007 Tsai et al.
(Continued)

FOREIGN PATENT DOCUMENTS

WO    WO 2010096720 A2 *  8/2010  ......... A61K 49/0032

OTHER PUBLICATIONS

Blanchard, S.C., et al., "tRNA dynamics on the ribosome during translation" Proc Natl Acad Sci USA (2004) pp. 12893-12898, vol. 35.
(Continued)

*Primary Examiner* — Aaron W Carter
(74) *Attorney, Agent, or Firm* — Scully, Scott, Murphy & Presser, P.C.

(57) ABSTRACT

Automatically selecting time traces from a fluorescence experiment, in one aspect, may include capturing results of the fluorescence experiment in a moving image; localizing sources of fluorescence in the moving image; producing time traces of each fluorescent source by monitoring fluorescence intensity of said localized sources in the moving image over time; removing unuseful time traces from said produced time traces; and selecting useful time traces from said produced time traces based on one or more defined criteria. FRET traces from selected time traces may be further calculated and analyzed. A unified computer-implemented platform in one aspect may include tools to locate single molecules, extract traces, classify smFRET traces according to adjustable parameters, and quantify the kinetic (Continued)

parameters of FRET transitions using analytical procedures such as Hidden Markov Modeling (HMM) procedures.

34 Claims, 17 Drawing Sheets

(75) Inventors: James Munro, New Haven, CT (US); Peter Geggier, New York, NY (US)

(56) References Cited

U.S. PATENT DOCUMENTS

| | | | | |
|---|---|---|---|---|
| 8,906,673 | B2* | 12/2014 | Vu | B82Y 15/00 435/288.7 |
| 2004/0099813 | A1* | 5/2004 | Eggeling | G01N 21/6408 250/459.1 |
| 2005/0048555 | A1* | 3/2005 | Holmes | G06T 7/0026 435/6.18 |
| 2007/0109536 | A1* | 5/2007 | Weiss | G01J 3/4338 356/318 |
| 2010/0193703 | A1 | 8/2010 | Kimura et al. | |
| 2010/0235105 | A1 | 9/2010 | Volkov et al. | |
| 2011/0180701 | A1* | 7/2011 | Woehl | B03C 5/00 250/282 |
| 2011/0256580 | A1* | 10/2011 | Kim | B01L 3/502784 435/29 |
| 2011/0281746 | A1* | 11/2011 | Chagovetz | C12Q 1/6813 506/9 |
| 2011/0294116 | A1* | 12/2011 | Huang | C12Q 1/6869 435/6.1 |
| 2012/0027689 | A1* | 2/2012 | Blanchard | A61K 49/0032 424/9.6 |
| 2012/0045748 | A1* | 2/2012 | Willson | C12Q 1/6804 435/5 |
| 2012/0129835 | A1* | 5/2012 | Brennand | A61K 31/519 514/211.13 |
| 2013/0122525 | A1* | 5/2013 | Blanchard | C07K 14/195 435/7.37 |
| 2013/0308842 | A1* | 11/2013 | Blanchard | G01N 21/6408 382/128 |
| 2014/0093870 | A1* | 4/2014 | Blanchard | G01N 33/542 435/6.1 |
| 2015/0166611 | A1* | 6/2015 | Blanchard | G01N 33/542 435/5 |

OTHER PUBLICATIONS

Bronson, J.E. et al., "Learning rates and states from biophysical time series: A Bayesian approach to model selection and single-molecule FRET data" Biophys J (2009) pp. 3196-3205, vol. 97, No. 12.
Cheezum, M.K. et al., "Quantitative comparison of algorithms for tracking single fluorescent particles" Biophys J (2001) pp. 2378-2388, vol. 81, No. 4.
Dave, R. et al., Mitigating Unwanted Photophysical Processes for Improved Single-Molecule Fluorescence Imaging Biophys J (2009) pp. 2371-2381, vol. 96, No. 6.
Dunkle, J.A. et al., "Structures of the bacterial ribosome in classical and hybrid states of tRNA binding" Science (2011) pp. 981-984, vol. 332, No. 6032.
Fei, J. et al., "Coupling of ribosomal L1 stalk and tRNA dynamics during translation elongation" Mol Cell (2008) pp. 348-359, vol. 30, No. 3.
Feldman, M.B. et al., "Aminoglycoside Activity Observed in Single, Pre-translocation ribosome complexes" Nature Chemical Biology (2009) pp. 54-62, vol. 6.
Fu, J. et al., "Cryoelectron microscopy structures of the ribosome complex in intermediate states during tRNA translocation" Proc Natl Acad Sci USA (2011) pp. 4817-4821, vol. 108, No. 12.
Geggier, P. et al., "Conformational Sampling of Aminoacyl-tRNA during Selection on the Bacterial Ribosome" J Mol Biol (2010) pp. 576-595, vol. 399, No. 4.
Haller, A. et al., "Conformational capture of the Sam-II riboswitch" Nat Chem Biol (2011) pp. 393-400, vol. 7, No. 6.
Joo, C. et al., "Single-Molecule FRET with Total Internal Reflection Microscopy" Single-Molecule Techniques: A Laboratory Manual. New York: Cold Spring Harbor Laboratory Press (2008).
Liu, Y. et al., "A comparative study of multivariate and univariate hidden Markov modelings in time-binned single-molecule FRET data analysis" J Phys Chem B (2010) pp. 5386-5403, vol. 114, No. 16.
McKinney, S.A. et al., "Analysis of Single-Molecule Fret Trajectories Using Hidden Markov Modeling" Biophys J (2006) pp. 1941-1951, vol. 91, No. 5.
Munro, J.B. et al., "Identification of two distinct hybrid state intermediates on the ribosome" Mol Cell (2007) pp. 505-517, vol. 25, No. 4.
Munro, J.B. et al., "A New View of Protein Synthesis: Mapping the Free Energy Landscape of the Ribosome Using Single-Molecule FRET" Biopolymers (2008) pp. 565-577, vol. 89, No. 7.
Qin, F., "Restoration of single-channel currents using the segmental k-means method based on hidden Markov modeling" Biophys J (2004) pp. 1488-1501, vol. 86, No. 3.
Qin, F. et al., "Estimating single-channel kinetic parameters from idealized patch-clamp data containing missed events" Biophys J (1996) pp. 264-280, vol. 70.
Qin, F. et al., "Maximum likelihood estimation of aggregated Markov processes" Proc Biol Sci (Mar. 1997) pp. 375-383, vol. 264, No. 1380.
Rabiner, L.R., "A Tutorial on Hidden Markov Models and Selected Applications in Speech Recognition" Proceedings of the IEEE (1989) pp. 257-286, vol. 77, No. 2.
Robbins, M.S. et al., "The Noise Performance of Electron Multiplying Charge Coupled Devices" IEEE Transactions on Electron Devices (2003) pp. 1227-1232, vol. 50, No. 5.
Roy, R. et al., "A practical guide to single-molecule FRET" Nat Methods (2008) pp. 507-516, vol. 5, No. 6.
Stryer, L. et al., "Energy transfer: a spectroscopic ruler" Proc. Natl. Acad. Sci., USA (1967) pp. 719-726, vol. 58, No. 2.
Walter, N.G. et al., "Do-it-yourself guide: how to use the modern single-molecule toolkit" Nat Methods (2008) pp. 475-789, vol. 5, No. 6.
Weiss, S., "Fluorescence spectroscopy of single biomolecules" Science (1999) pp. 1676-1683, vol. 283, No. 5408.
Zhao, Y. et al., "Single-molecule dynamics of gating in a neurotransmitter transporter homologue" Nature (2010) pp. 188-193, vol. 465, No. 7295.
Zhao, Y. et al., "Substrate-modulated gating dynamics in a Na+-coupled neurotransmitter transporter homologue" Nature (2011) pp. 109-113, vol. 474, No. 7349.
Zhuang, X., "Single-molecule RNA science" Annu Rev Biophys Biomol Struct (2005) pp. 399-414, vol. 34.
International Search Report dated Sep. 12, 2012 issued in International Application No. PCT/US2012/022875.

* cited by examiner

COMPUTER-IMPLEMENTED PLATFORM FOR AUTOMATED FLUORESCENCE IMAGING AND KINETIC ANALYSIS

CROSS-REFERENCE TO RELATED APPLICATIONS

This application claims the benefit of U.S. Provisional Application No. 61/437,203, filed on Jan. 28, 2011, which is incorporated by reference herein in its entirety.

STATEMENT REGARDING FEDERALLY SPONSORED RESEARCH OR DEVELOPMENT

This invention was made with Government support under Grant Number 1R01GM079238-01 awarded by the National Institutes of Health. The United States Government has certain rights in the invention.

FIELD

The present invention generally relates to fluorescence imaging techniques and analysis, and more particularly to computer system and software platform for automated fluorescence imaging, e.g., FRET imaging and kinetic analysis.

BACKGROUND

Single-molecule fluorescence imaging techniques enable the detection of individual dye-labeled proteins and nucleic acids in vitro and in vivo (for example, see Walter, N. G., C. Y. Huang, A. J. Manzo, and M. A. Sobhy. 2008. Do-it-yourself guide: how to use the modern single-molecule toolkit. *Nat Methods* 5 (6):475-89 (Walter et al. 2008); Zhuang, X. 2005. Single-molecule RNA science. *Annu Rev Biophys Biomol Struct* 34:399-414 (Zhuang 2005); Weiss, S. 1999. Fluorescence spectroscopy of single biomolecules. *Science* 283 (5408):1676-83 (Weiss 1999); and Roy, R., S. Hohng, and T. Ha. 2008. A practical guide to single-molecule FRET. *Nat Methods* 5 (6):507-16 (Roy et al. 2008)). Such methods can be used in conjunction with Fluorescence Resonance Energy Transfer (FRET), where through-space energy transfer between two fluorophores— donor and acceptor—can be used to report on the distance between the two probes. More than two fluorophores may be used, such that multiple FRET pairs can interact in a given system. FRET is a spectroscopic ruler (for example, see Stryer, L., and R. P. Haugland. 1967. Energy transfer: a spectroscopic ruler. *Proc. Natl. Acad. Sci., USA* 58 (2):719-26 (Stryer et al. 1967)), providing a means to measure the structural properties of biological particles. Using surface-immobilization to restrict diffusion, this structural information can be followed over time, revealing structural dynamics involved in the molecular mechanisms of biological motors, transporters, sensors, signaling networks, and enzymes.

Because the observed dynamics often manifest as a sequence of dwells in distinct FRET states, single-molecule FRET (smFRET) traces are amenable to hidden Markov modeling (HMM) analysis provided that certain simplifying assumptions can be made (for example, see Rabiner, L. R. 1989. A Tutorial on Hidden Markov Models and Selected Applications in Speech Recognition. *Proceedings of the IEEE* 77 (2):257-286 (Rabiner 1989)). This analysis provides a statistical framework for evaluating kinetic models that describe the energy landscape of motion (for example, see McKinney, Sean A., Chirlmin Joo, and Taekjip Ha. 2006. Analysis of Single-Molecule FRET Trajectories Using Hidden Markov Modeling. *Biophys J* 91 (5):1941-1951 (McKinney et al. 2006); Munro, J. B., R. B. Altman, N. O'Connor, and S. C. Blanchard. 2007. Identification of two distinct hybrid state intermediates on the ribosome. *Mol Cell* 25 (4):505-17 (Munro et al. 2007); Bronson, Jonathan E., Jingyi Fei, Jake M. Hofman, Ruben L. Gonzalez Jr., and Chris H. Wiggins. 2009. Learning rates and states from biophysical time series: A Bayesian approach to model selection and single-molecule FRET data. *Biophys J* 97 (12): 3196-3205 (Bronson et al. 2009); and Liu, Y., J. Park, K. A. Dahmen, Y. R. Chemla, and T. Ha. 2010. A comparative study of multivariate and univariate hidden Markov modelings in time-binned single-molecule FRET data analysis. *J Phys Chem B* 114 (16):5386-403 (Liu et al. 2010)).

In aggregate, thousands of traces may provide enough statistical information to reveal subtle changes in structure and dynamics in response to ligands, drugs, or interactions with binding partners not readily apparent in individual traces (for example, see Feldman, M. B, D. S. Terry, R. B. Altman, and S. C. Blanchard. 2009. Aminoglycoside Activity Observed in Single, Pre-translocation ribosome complexes. *Nature Chemical Biology* 6, 54-62 (Feldman et al. 2009); and Geggier, P., R. Dave, M. B. Feldman, D. S. Terry, R. B. Altman, J. B. Munro, and S. C. Blanchard. 2010. Conformational Sampling of Aminoacyl-tRNA during Selection on the Bacterial Ribosome. *J Mol Biol* 399(4): 576-95 (Geggier et al. 2010)).

Analysis of smFRET data presents a problem because many current analysis methods depend on manual steps like examining each trace by eye. As a result, data analysis presents a significant bottleneck for throughput. Manual data analysis techniques can also introduce biases that that may in some cases be user dependent leading to altered or misguided interpretations of the data obtained.

In the present disclosure, we report a software platform for smFRET investigations that circumvents the throughput limits of manual analysis steps through automation.

SUMMARY

The present disclosure provides for automated analysis of fluorescence experiments, e.g., smFRET experiments. In one aspect, a method is provided to automatically select time traces from a fluorescence experiment. The method may include capturing results of the fluorescence experiment in a moving image. The method may also include localizing sources of fluorescence in the moving image. The method may further include producing time traces of each fluorescent source by monitoring fluorescence intensity of said localized sources in the moving image over time. Still yet, the method may include removing unuseful time traces from said produced time traces. The method may further include selecting useful time traces from said produced time traces based on one or more defined criteria.

In yet another aspect, an automated system for analysis of data from smFRET experiments may be provided. The automated system may include a time trace selection module operable to execute on a processor and further operable to capture results of the smFRET experiment in a moving image. The time trace selection module may be further operable to localize sources of fluorescence in the moving image and produce time traces of each fluorescent source by monitoring fluorescence intensity of said localized sources in the moving image over time. The time trace selection module may be further operable to remove unuseful time traces from said produced time traces, and select useful time traces from said produced time traces based on one or more defined criteria. The automated system may also include a time trace analysis module operable to calculate FRET traces from the useful time traces, and further operable to analyze the FRET traces.

A computer readable storage medium storing a program of instructions executable by a machine to perform one or more methods described herein also may be provided.

Further features as well as the structure and operation of various embodiments are described in detail below with reference to the accompanying drawings.

DETAILED DESCRIPTION

Figure 1:
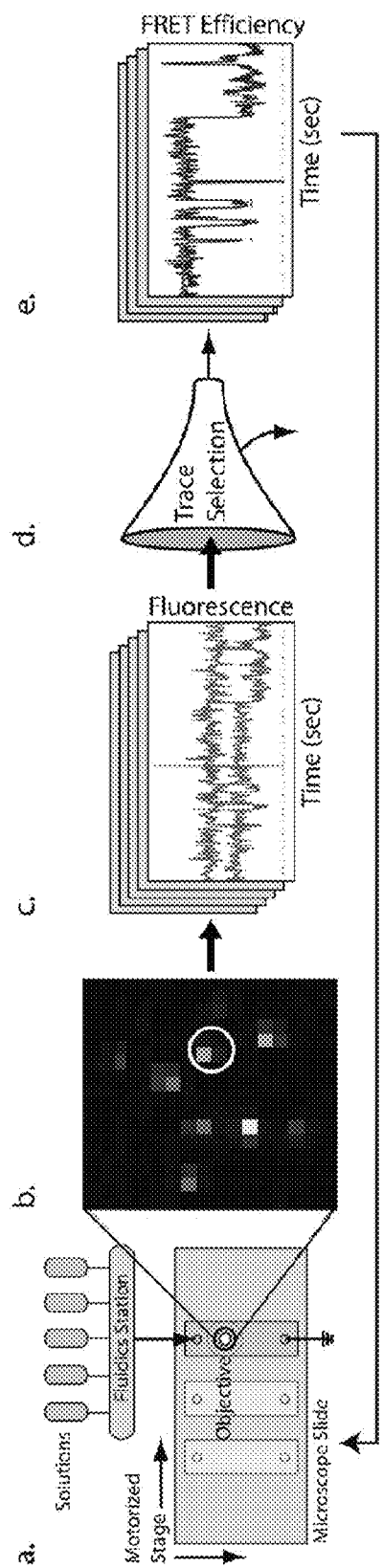
FIG. 1 illustrates a schematic of the automated smFRET data analysis pipeline in one embodiment of the present disclosure. (a) Dye-labeled samples surface-immobilized within a microfluidic imaging chamber are illuminated via Total Internal Reflection (TIR). (b) Single fluorophore pairs are localized in wide-field fluorescence movies. (c) Fluorescence intensity over each fluorophore's point-spread function is summed over time to yield fluorescence traces. (d) A subset of traces is then selected according to defined selection criteria. (e) FRET traces are calculated from fluorescence traces and then analyzed using hidden Markov modeling procedures to assign the state of the system at each point in time and estimate kinetic parameters.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

smFRET imaging experiments provide a powerful means for direct observation of the dynamic properties of individual proteins and nucleic acids. The software platform presented here enhances the throughput of smFRET imaging and minimizes the need for user interaction, while maintaining accuracy, robustness to experimental noise, and sensitivity. Each analysis procedure was optimized using simulated smFRET data. In contrast to trace-by-trace visual inspection, automated selection enables biasing effects to be quickly and reproducibly evaluated, and systematically reduced or eliminated.

Complex biological complexes composed of many individual components, such as the ribosome, are more likely to be heterogeneous, and this non-uniformity may be biologically important. Because of its capacity to interrogate particles individually, smFRET techniques are ideally suited to investigate intrinsically heterogeneous populations. Thus, imaging strategies that increase observation times prior to photobleaching and analysis tools that can distinguish distinct subpopulations of particles are important to understanding such complex systems.

In one embodiment of the present disclosure a software platform is presented for single-molecule FRET (smFRET) investigations that circumvents the throughput limits of manual analysis steps through automation.

First, particles are detected and the fluorescence intensity is monitored to produce FRET-time traces. The particles may be surface-immobilized. The particle may be a protein, a nucleic acid molecule, a vesicle or other artificial membrane mimicking object, or a cell or tissue. The particle being analyzed may have multiple components, for example without limitation, a ribosome (itself comprised of RNA and protein), tRNA, amino acids, and mRNA. The particle also may be referred to herein as a system. Previously experimental noise has necessitated manual examination of these traces to select analyzable features and avoid artifacts. This process is time consuming and may have unintended consequences, including user bias, due to the exclusion of potentially informative behaviors in the ensemble. Frequently, the selected data are then used for fitting kinetic models, most often with hidden Markov modeling (HMM) methods that facilitate kinetic analysis (for example, see McKinney et al. 2006; Munro et al. 2007; Bronson et al. 2009; and Liu et al. 2010).

The software platform (schematized in FIG. 1), includes algorithms to perform these steps automatically and integrates HMM analysis tools so that the entire process can be performed with minimal to no user interaction. Analysis parameters can be tuned according to need and tools are available for detailed examination of the data, including manual selection.

The software platform of the present disclosure in one embodiment avoids the problem of moving data between multiple software packages with incompatible file formats. The analysis procedures in the software pipeline were validated and optimized using simulated fluorescence traces and wide-field movies that closely approximate experimental data. The use of simulations allows the direct comparison of the "true" kinetic parameters with analytical estimates.

In one embodiment of the present disclosure, results may be obtained in real time with experiments, enabling interpretation that can inform future experiments. Automation also enables consistent application of well-defined methods and selection criteria, which minimizes possible user bias and variability. The analysis methods are applicable to a wide range of biological systems and questions.

As a practical consequence of automation, results can be presented in real-time, or following an experiment. This rapid availability of experimental results may also facilitate the design of further experiments, enabling a rapid hypothesis-testing methodology.

By monitoring results as they are updated with each additional movie, the user can save time by discovering and correcting problems with the experiment earlier. The user can also determine when enough data have been acquired to pass predefined requirements for number of picked traces and/or error in parameter estimates.

Tight integration with the other analytical software, for example without limitation, the QuB analysis software package from State University of New York at Buffalo, enables the user to examine data with alternative models with more aggregated states and/or different connectivity using the same algorithms used in automated analysis. The analysis platform augments other analytical software such as QuB implementations by displaying fluorescence traces alongside FRET traces to provide context for the interpretation of smFRET data.

Since function may be regulated by changes in the kinetic landscape of enzyme conformation (for example, see Munro, J. B., A. Vaiana, K. Y. Sanbonmatsu, and S. C. Blanchard. 2008. A New View of Protein Synthesis: Mapping the Free Energy Landscape of the Ribosome Using Single-Molecule FRET. *Biopolymers* 89 (7):565-577 (Munro et al. 2008)), analytic equipment paired with the subject method may be used to uncover novel drugs or protein factors that regulate function.

For example, the analysis platform presented here was employed to examine the effects of aminoglycoside antibiotics on the kinetic landscape of tRNA motions and the role of these changes in translocation inhibition (for example, see Feldman et al. 2009). The demonstrated sensitivity and minimal bias of the analysis method works very well for detecting potentially subtle effects induced by a lead compound, as was observed for aminoglycoside binding to wild-type ribosomes.

Automated analysis may also prove valuable in any research context in a situation where dynamics of a system are studied. For instance, the automated analysis system may be used in screening a panel of conditions that stabilize intermediate states for structure determination using cryogenic electron microscopy and crystallography (for example, see Munro et al. 2008; Fu, J., Munro, J. B., Blanchard, S. C., Frank, J. 2011. Cryoelectron microscopy structures of the ribosome complex in intermediate states during tRNA translocation. *Proc Natl Acad Sci USA* 108 (12): 4817-21, (Fu et al. 2011); Dunkle, J. A., Wang, L., Feldman, M. B., Pulk, A., Chen, V. B., Kapral, G. J., Noeske, J., Richardson, J. S., Blanchard, S. C., Cate, J. H. Structures of the bacterial ribosome in classical and hybrid states of tRNA binding. 2011. Science 332(6032): 981-4, (Dunkle et al. 2011)). Likewise, this approach may also prove useful for optimizing conditions that shift the timescale of conformational motions to an experimentally accessible regime, as was the case in early ribosome smFRET experiments (for example, see Blanchard, S. C., H. D. Kim, R. L. Gonzalez, Jr., J. D. Puglisi, and S. Chu. 2004. tRNA dynamics on the ribosome during translation. *Proc Natl Acad Sci USA* 101 (35):12893-8 (Blanchard et al. 2004); Zhao, Y., D. Terry, L. Shi, H. Weinstein, S. C. Blanchard, and J. A. Javitch. 2010. Single-molecule dynamics of gating in a neurotransmitter transporter homologue. *Nature* 465 (7295):188-93 (Zhao et al. 2010); and Zhao, Y., D. Terry, L. Shi, H. Weinstein, S. C. Blanchard, and J. A. Javitch. 2011. Single-molecule dynamics of gating in a neurotransmitter transporter homologue. *Nature* 474 (7349):109-113 (Zhao et al. 2011)).

The software platform of tools of the present disclosure may be applicable to a wide range of biological systems and has already been used for imaging ribosome dynamics (for example, see Feldman et al. 2009 and Geggier et al. 2010), conformational rearrangements in membrane transport proteins (for example, see Zhao et al. 2010 and Zhao et al. 2011) and riboswitch regulatory elements present in messenger RNA (for example, see Haller, A., Rieder, U., Aigner, M., Blanchard, S. C., Micura, R. Conformational capture of the SAM-II riboswitch. 2011. *Nat Chem Biol* 7(6): 393-400 (Haller et al. 2011)). The software platform of tools of the present disclosure in one embodiment allows for selection criteria that can be easily added and modified according to the characteristics of the data, the types of artifacts observed, and the specific question at hand.

The kinetic analysis tools are also customizable and can be applied to more complex systems with aggregated states and complex connectivity (for example, see Qin, F., A. Auerbach, and F. Sachs. 1996. Estimating single-channel kinetic parameters from idealized patch-clamp data containing missed events. *Biophys J* 70:264-280, 1997. Maximum likelihood estimation of aggregated Markov processes. *Proc Biol Sci* 264 (1380):375-83 (Qin et al. 1996, 1997)). The simple, user-friendly interface to this software package minimizes the need for expert knowledge and user training which are required for traditional analysis methods, especially manual data selection and shuttling data amongst multiple data processing software packages. This advance helps lower the barrier to entry for performing single-molecule fluorescence experiments and ultimately encourage growth in the field.

Single Molecule Detection and Extracting Fluorescence Traces.

Figure 13:
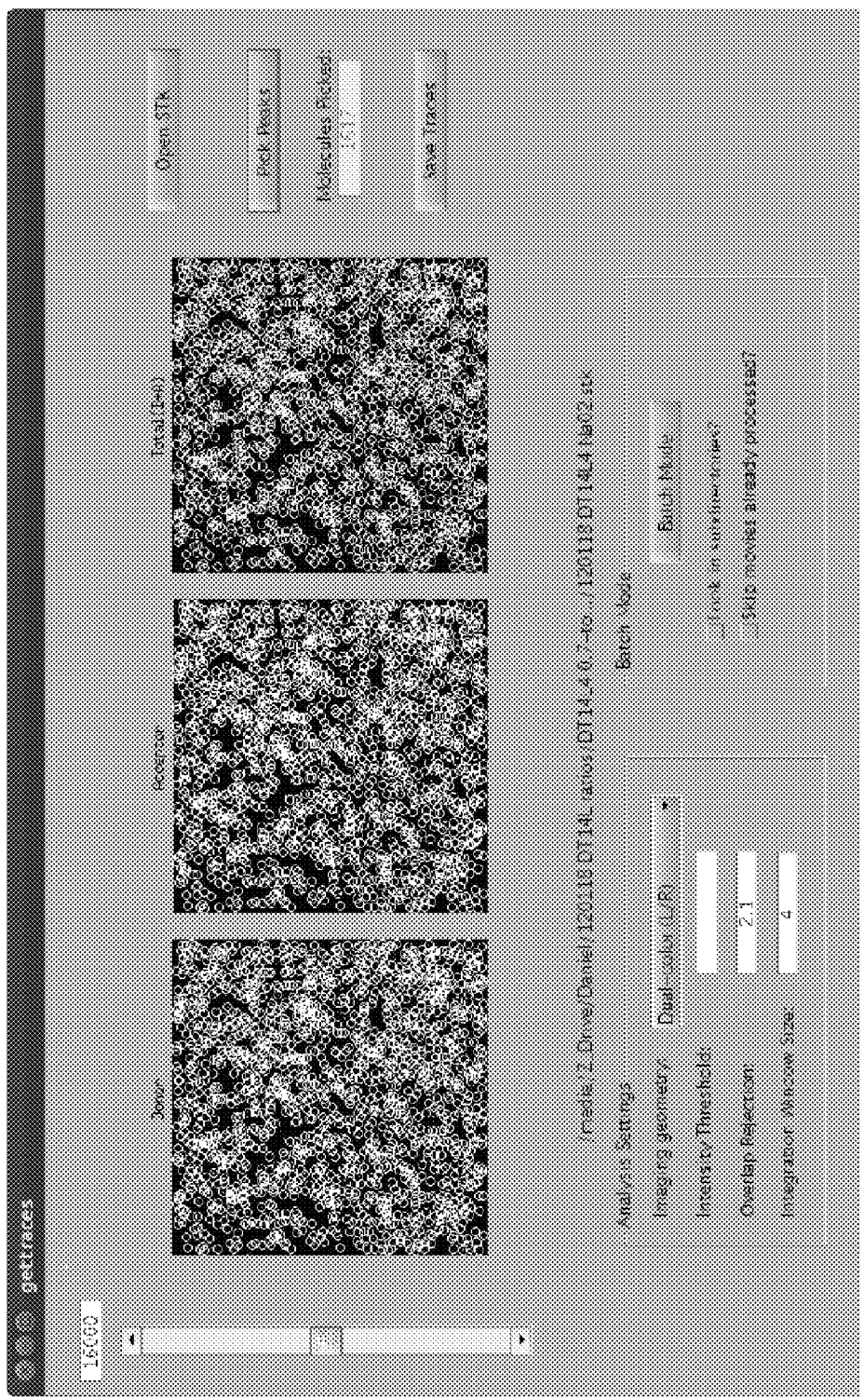
FIG. 13 illustrates UI for software that extracts fluorescence traces from experimental wide-field movies of dye-labeled samples in one embodiment of the present disclosure.

FIG. 13 illustrates an example UI for software that implements the methods described in this section. In one embodiment of the present disclosure, default parameters are provided that are considered to be effective for commercially available imaging systems, but are user tunable and can be computed automatically from the data.

Investigating the properties of single molecules involves their localization. Such algorithms have been developed for single-particle tracking (for example, see Cheezum, M. K., W. F. Walker, and W. H. Guilford. 2001. Quantitative comparison of algorithms for tracking single fluorescent particles. *Biophys J* 81 (4):2378-88 (Cheezum et al. 2001)). One of the simplest approaches is to scan the field of view for intensity maxima crossing a set threshold:

$$I_{Threshold} = N_{Threshold} \times \text{stdev}(I_{BG}). \quad (1)$$

where $I_{Threshold}$ represents intensity maxima crossing a threshold, $I_{BG}$ represents average background intensity, $N_{Threshold}$ represents a sensitivity parameter, where higher values only detect peaks that are very bright compared to background noise and lower values can detect very weak signals, but may also produce many false positives.

For a single threshold value to be effective for removal of background, the background should have uniform intensity, but this is often not the case experimentally. To flatten background intensity, an image that approximates the gross features of the background is generated by smoothing the lowest intensity (unpopulated) regions of the field and this image is subtracted. In one embodiment of the present disclosure, background intensity data ($I_{BG}$) is collected from unpopulated (background) regions at the end of each movie and is subtracted from the field-of-view image prior to peak detection.

In wide-field FRET imaging experiments, fluorescence information from each particle is distributed over multiple channels (e.g., two: donor and acceptor, or more than two channels). For particle localization, it is useful to sum images from all channels because this makes selection largely independent of the fluorescence characteristics of the particular system. The channels should be precisely aligned. If this is not possible in hardware, software mapping functions may be utilized (for example, see Roy et al. 2008). This method can be expanded to multiple imaging geometries, including 1, 2, 3, 4 or more channels (e.g., colors).

Figure 2:
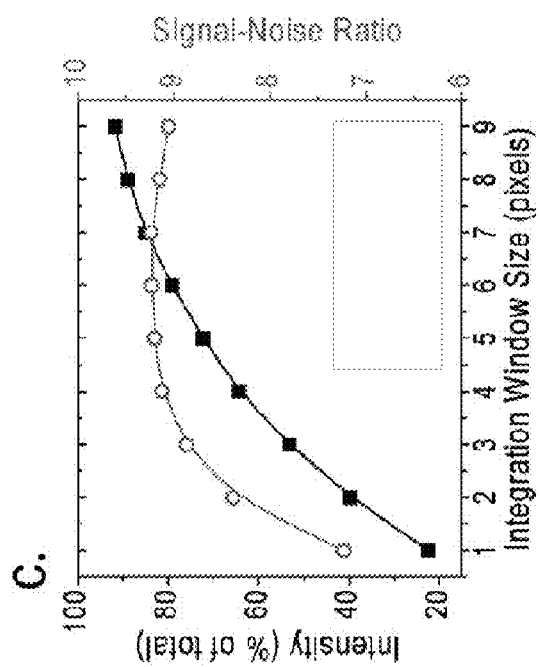
FIG. 2 illustrates single-molecule localization and trace generation methods in one embodiment of the present disclosure. Wide-field fluorescence movies were simulated with fluorophores placed at widely-separated, semi-random locations and the intensity of each was distributed across a 2D Gaussian point-spread function (PSF). (a) An example simulated movie is shown, where fluorophore locations (white circles) are determined by finding intensity maxima that cross a defined threshold. (b) The intensity from each fluorophore is collected over an integration window (outlined in white for an example peak), capturing some fraction of the total intensity. (c) Total integrated intensity as a percent of true intensity (filled black squares) and signal-noise ratios (open gray circles) is shown as a function of the size of the integration window.
Figure 2:
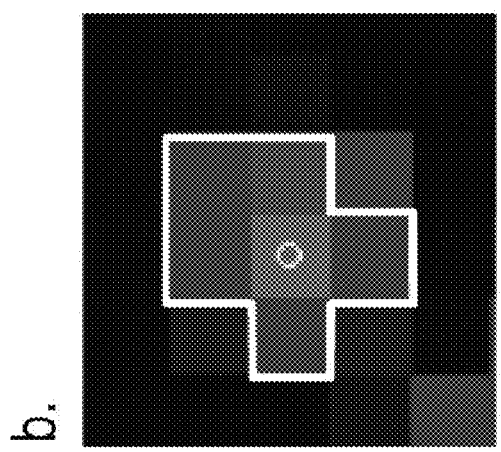
Figure 2:
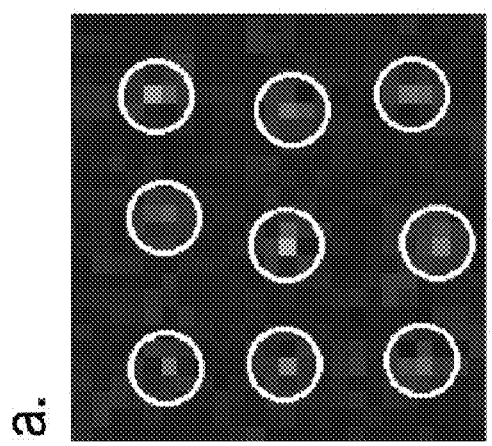

To evaluate detection accuracy, this method was applied to simulated wide-field movies with fluorophores placed at widely-separated locations (FIG. 2a). The effects of background noise were approximated by adding intensity from experimental movies acquired in the absence of immobilized fluorophores. Using simulation parameters that approximate our experimental data, $N_{Threshold}=8$ yielded optimal results: >95% of simulated fluorophores were correctly located within 1 pixel with a false-positive rate <0.2%.

Integration Window. Integration window refers to an image area, e.g., number of pixels. Fluorescence traces can be extracted from each localized particle by monitoring the fluorescence intensity over time. Experimentally, the intensity of each fluorophore is distributed across a roughly-Gaussian point spread function (PSF) with a symmetric standard deviation ($\sigma_{PSF} \approx 0.8$ pixels in our experiments, FIG. 2b). Summing over many pixels can recover >90% of the intensity in simulated movies, but each additional pixel also introduces background noise (FIG. 2c). Optimal signal-noise ratios were observed when summing over an integration window set at 4 pixels ($5 \times \sigma_{PSF}$, where ~60% of the intensity is collected).

While the value of $\sigma_{PSF}$ varies with the experimental setup, this procedure provides a general way to define an optimal window size that maximizes signal-noise ratios. The number can be automatically discovered by calculating the average signal-noise ratio (signal magnitude divided by the standard deviation of the fluorescence signal) across a range of values (preferably 1-9 pixels, but the range may be set based on the user's criteria) and finding the maximum.

Figure 3:
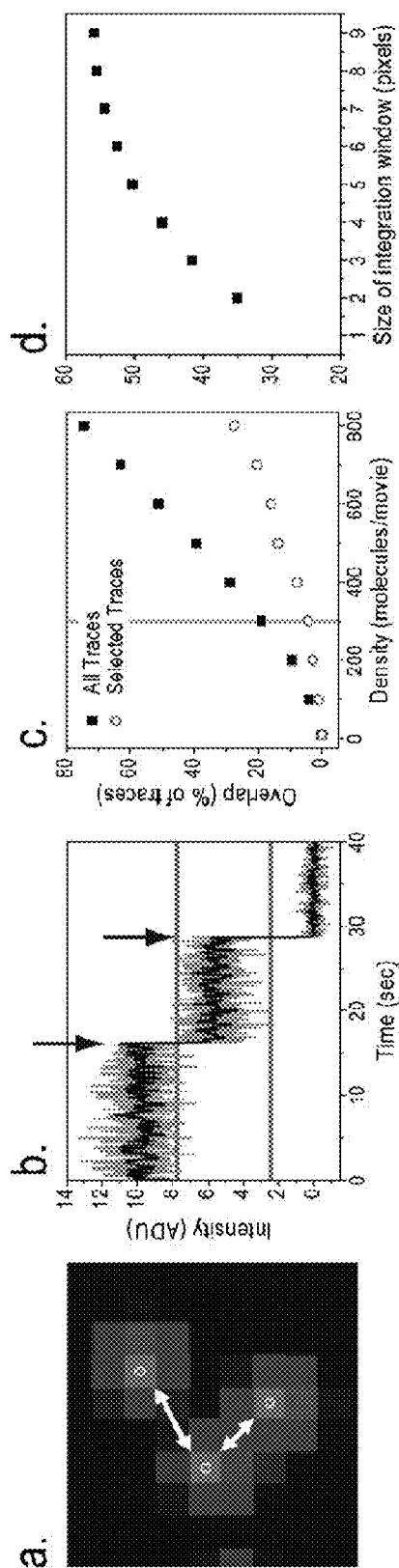
FIG. 3 illustrates methods for avoiding signal contamination due to overlapping point-spread functions in one embodiment of the present disclosure. Wide-field movies are simulated with randomly positioned fluorophores. (a) Some point-spread functions (PSF) stochastically overlap and can be detected in most cases by the distance between intensity peaks (white arrows). (b) When fluorescence from multiple particles is summed, multi-step photobleaching may be observed (marked by black arrows). These steps were detected by median filtering the fluorescence intensity (black vs. gray lines) and finding sharp intensity drops that cross a threshold (horizontal lines at intensity of 2 and 8). (c) Movies were simulated with varying density of particles. The percentage of traces with >15% signal contamination resulting from PSF overlap is shown for movies simulated with varying fluorophore density (filled black squares) and after processing with the automated overlap rejection algorithm (open gray circles). (d) The percentage of traces with signal contamination was also measured over a range of integration window sizes used for trace generation (300 molecules/field).

Methods for removing unuseful traces, including methods for minimizing signal contamination caused by overlapping point-spread functions:

Because surface immobilization of dye-labeled particles is generally random, PSFs stochastically overlap (FIG. 3a). When the intensity is summed from any such PSF, the resulting fluorescence trace may be contaminated by intensity from nearby particles, making it unsuitable for analysis (for example, see Roy et al. 2008). Such traces have elevated total intensity ($I_D+I_A$) and characteristic multi-step drops in intensity as each contributing fluorophore photobleaches (FIG. 3b). The percentage of contaminated traces increases dramatically with the density of fluorophores (FIG. 3c, black squares). Although signal contamination is reduced at very low densities, experimental throughput would be adversely affected. Even in movies simulated with a relatively low density of 300 fluorophores per field (0.24 $\mu m^{-2}$), over half of the traces have significant (>15%) contamination with nearby fluorescence signals.

To maximize yield while minimizing signal contamination, a method of the present disclosure in one embodiment may specifically identify contaminated traces based on three criteria. Distinct peaks of intensity are rejected if their centroids are closer than an established threshold, in this case $3 \times \sigma_{PSF}$ (which in this case is 2.4 pixels). The centroid is the center of the PSF distribution, e.g., approximated by finding the weighted average position of the PSF distribution (where the weights are the intensities). Other methods such as fitting to a Gaussian distribution could also be employed. The factor by which $\sigma_{PSF}$ is multiplied is preferably 1-9, but the range may be set based on the user's criteria. This step reduces the percentage of contaminated traces from 50% to 23%. The remaining fraction of contamination primarily is mainly attributable to multiple molecules within a diffraction-limited area and thus not readily distinguishable as multiple peaks of intensity in the field-of-view. Traces resulting from these peaks were detected and removed if their average total intensity was more than two standard deviations from the mean. Such traces were also detected by median filtering the total fluorescence signal (the sum of the fluorescence signal from all channels at each point in time) to reduce noise and finding large drops in intensity that do not return to previous levels (FIG. 3b).

"Large" with respect to "large drops" is defined as follows. The total fluorescence signal (the sum of the fluorescence signal from all channels at each point in time) of each trace is median filtered (time window size may for example be 9 frames). A median filter is used because it preserves large changes in intensity but removes most high-frequency noise. We then take the gradient of this filtered trace (this is a trace showing the magnitude of changes in the filtered signal). Any instance where the gradient drops below a threshold is considered a bleaching event. In one embodiment of the present disclosure, for example, the threshold is calculated as 8 standard deviations of the gradient signal.

Together, these strategies reduced the percentage of contaminated traces to <4%. Significant improvements were observed at all densities evaluated (FIG. 3c, circles). Since the level of signal contamination is also directly related to the size of integration window (FIG. 3d), the integration window size should be as small as possible without sacrificing signal-noise ratios (FIG. 2c).

Other strategies for removing unhelpful traces may include:

i) Identifying and removing frames with saturated intensity. This describes the number of frames of a trace where the total fluorescence intensity falls above the detection limit (32,000 arbitrary units), resulting in a loss of information.

Useful range: 0-10,000
Optimal value: 5 ii) Standard deviation of background. This describes the degree of noise in the background after the donor dye photobleaches. High noise levels may indicate multiple donor fluorophores, incorrect background subtraction, and high levels of surface fluorescence that fades over time. Note: SNR1 (signal to background noise ratio) uses a different measure of background noise—standard deviation of the first 50 frames after bleaching. This captures most of the intrinsic background noise, but not slow drifting changes or occasional spikes of intensity.

Useful range: 300-5,000
Optimal value: 1,500

Selecting Useful smFRET Traces:

The data extracted from wide-field movies represents an ensemble of many traces with potentially distinct properties. This stochastic variability can be exploited to isolate traces with the most ideal behaviors, including low noise, long lifetime before photobleaching, and the appearance of dwells in clearly distinct states. The data may also contain traces corresponding to fluorescent impurities on the surface (FIG. 7), sample aggregates, and optical artifacts that need to be eliminated before further analysis. Historically, selection of smFRET data has been achieved through visual inspection of each trace (for example, see Munro et al. 2007; Blanchard et al. 2004; and Fei, J., P. Kosuri, D. D. MacDougall, and R. L. Gonzalez, Jr. 2008. Coupling of ribosomal L1 stalk and tRNA dynamics during translation elongation. *Mol Cell* 30 (3):348-59 (Fei et al. 2008)). As acquisition throughput has increased and experiments have grown more complex, this process has become a significant bottleneck. In addition, great care should be taken to ensure consistent and unbiased trace selection to minimize analytical variability.

Figure 8:
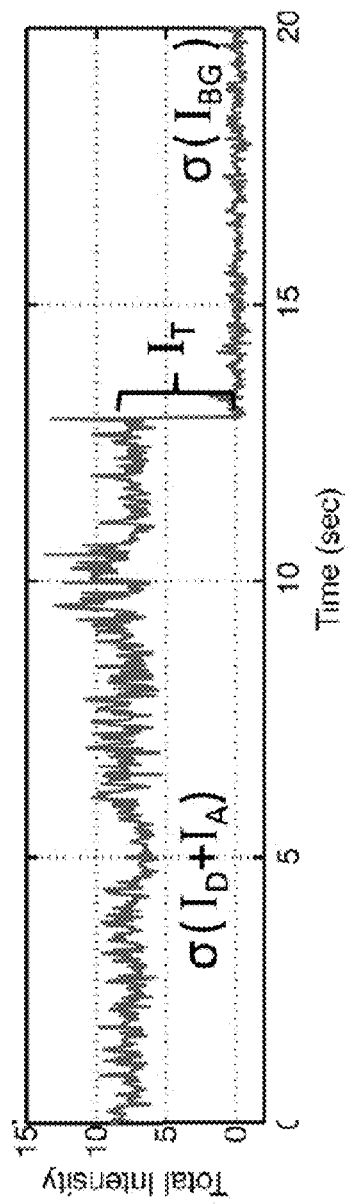
FIG. 8 are diagrams illustrating the standard selection criteria used in our automated smFRET trace selection method in one embodiment. Signal-to-Noise ratios can be calculated as mean total intensity ($I_T=<I_D+I_A>$) relative to either the standard deviation of background intensity ($\sigma(I_{BG})$) or standard deviation of fluorescence intensity prior to photobleaching ($\sigma(I_A+I_D)$).
Figure 14:
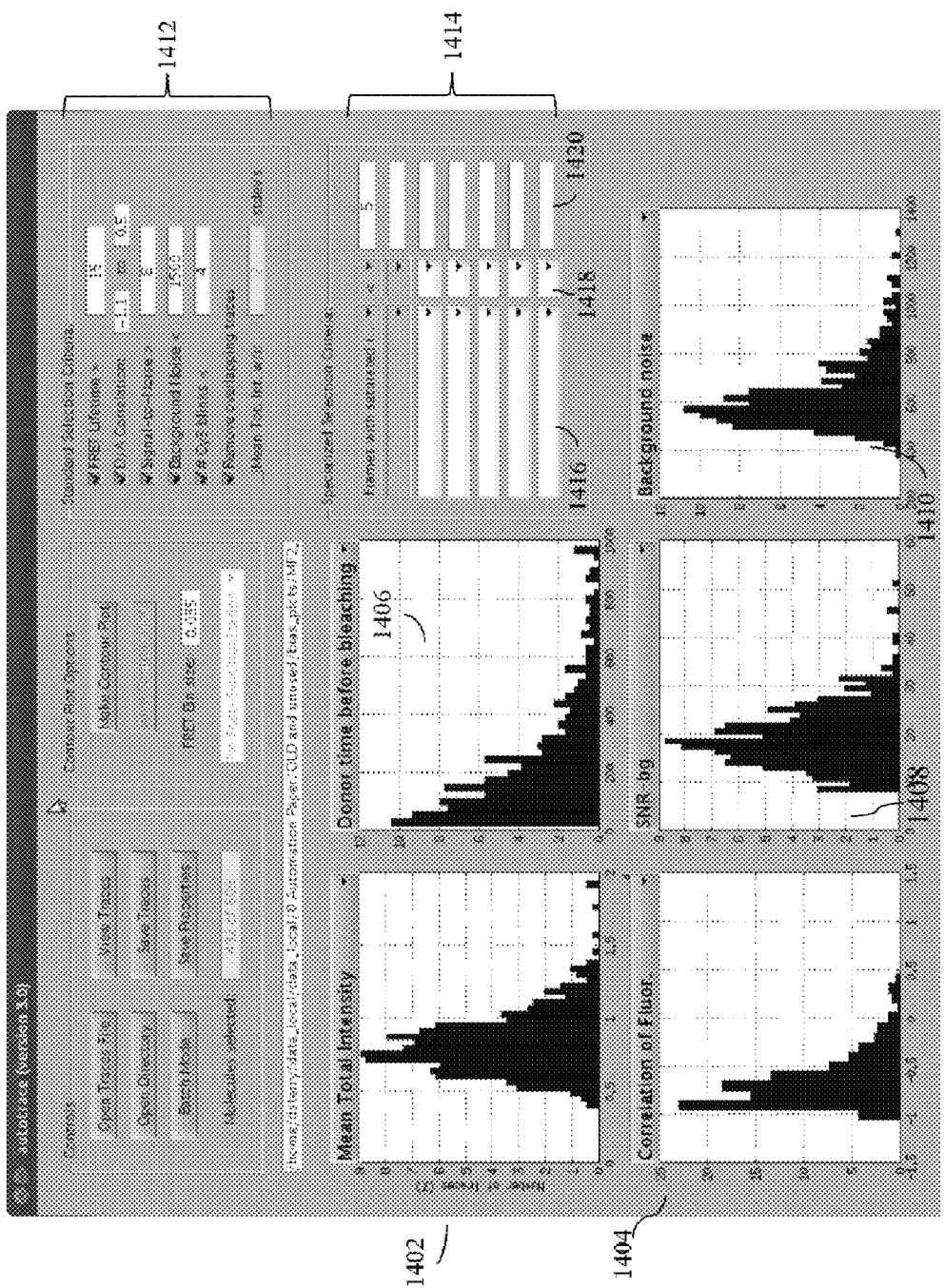
FIG. 14 illustrates UI for software that selects only traces meeting specified criteria in one embodiment of the present disclosure.

FIG. 14 illustrates an example UI for software or automated system that implements the methods described in this section that facilitates rapid, robust examination and selection of smFRET traces. In one embodiment of the present disclosure, trace properties are defined that describe essential characteristics; both for quantifying usefulness and the identification of specific artifacts. Signal-noise ratios (SNR) describe trace quality, where signal is the magnitude of total fluorescence intensity ($I_{total}=I_D+I_A$) and noise is the standard deviation of background (SNR1) or total fluorescence intensity (SNR2) (FIG. 8). FRET Lifetime ($LT_{FRET}$) describes the observation time in a trace and is defined as the number of frames showing FRET significantly above background levels (E>0.13). Stochastic fluctuations in background intensity may occasionally result in FRET values above the threshold. To reduce the contribution of such artifacts to the final calculation of lifetime, runs of less than 5 frames above background are not considered in the calculation in one embodiment of the present disclosure.

Additional criteria were defined to specifically identify dye-labeled samples from background noise and fluorescent contaminants. Anti-correlation between donor and acceptor fluorescence intensity is a key characteristic of FRET data, where changes in one fluorophore's emission intensity should be reflected by opposing changes in the other. This property is particularly important for manual trace selection. Pearson's correlation coefficient over the raw fluorescence traces can be used to quantify the degree of anti-correlation. Alternatively, correlation may be calculated using the derivatives of fluorescence traces ($CC_{\Delta D,\Delta A}$) (for example, see Fei et al. 2008), which focuses on transitions between distinct FRET states. Donor dyes typically employed for smFRET imaging (e.g., Cy3) are highly photostable, only rarely making transitions to non-fluorescent dark states (blinking) (for example, see Roy et al. 2008; Dave, R., D. S. Terry, J. B. Munro, and S. C. Blanchard. 2009. Mitigating Unwanted Photophysical Processes for Improved Single-Molecule Fluorescence Imaging. *Biophys J* 96 (6):2371-2381 (Dave et al. 2009); and Joo, C., and T. Ha. 2008. Single-Molecule FRET with Total Internal Reflection Microscopy. In *Single-Molecule Techniques: A Laboratory Manual*. New York: Cold Spring Harbor Laboratory Press (Joo et al. 2008)). The number of blinking events ($N_{Blinks}$) is therefore useful in specifically identifying dye-labeled samples. The system may include libraries with data concerning blinking events. For example and without limitation, the library may correlate specific dyes to specific blink rates in various conditions, and the system may ask for user input at the beginning of the experiment regarding protocol and reagents.

The highest FRET value observed in a trace ($E_{max}$) can be used to distinguish subsets of data with low average FRET values that never sample the expected FRET states. Most traces for a particular system would be expected to sample back and forth between a few distinct FRET states (say, E=0.5 and E=0.8). If there is a subset of traces with FRET values that are never in that range (0.5-0.8), they are probably not the molecules of interest. This is tested in one embodiment by calculating the highest FRET value observed in a trace (say 0.3). If it is lower than an expected minimum based on prior knowledge of the system (0.5 following the example just provided), then it is removed.

Positive selection criteria may include:
adequate signal-noise ratio (SNR)
In a preferred embodiment, higher than threshold of 8 (SNR1)
range: 5-40
FRET Lifetime
In a preferred embodiment, higher than or equal to threshold: 15 frames
range: 0-10,000 (can be zero when there is no discrete photobleaching) event
degree of anti-correlation
In a preferred embodiment, less than or equal to threshold of 0.5
range: −1.0 to 1.0
number of blinking events
In a preferred embodiment, less than or equal to threshold of 3
range: 0 to 100
number of donor photobleaching events
In a preferred embodiment, less than or equal to threshold of 1
range: 0 to 10 (zero meaning no discrete photobleaching events were detected)
highest FRET value observed in a trace
In a preferred embodiment, greater than or equal to threshold of 0.3
range: 0 to 1.0
FRET traces may be calculated as follows in one embodiment of the present disclosure. In single-molecule FRET experiments, a ratiometric measure of distance between the two dyes (FRET efficiency, FRET) may be calculated at each point in time from the fluorescence traces according to the following equation:

$$E_{FRET}(t) = \frac{A(t)}{[A(t)+D(t)]}. \qquad (2)$$

where at each time t, $E_{FRET}$ is the efficiency of energy transfer (FRET), A is the acceptor fluorescence trace, and D is the donor fluorescence. Multiple FRET traces could be generated in cases where more than two dyes are employed.

Figure 7:
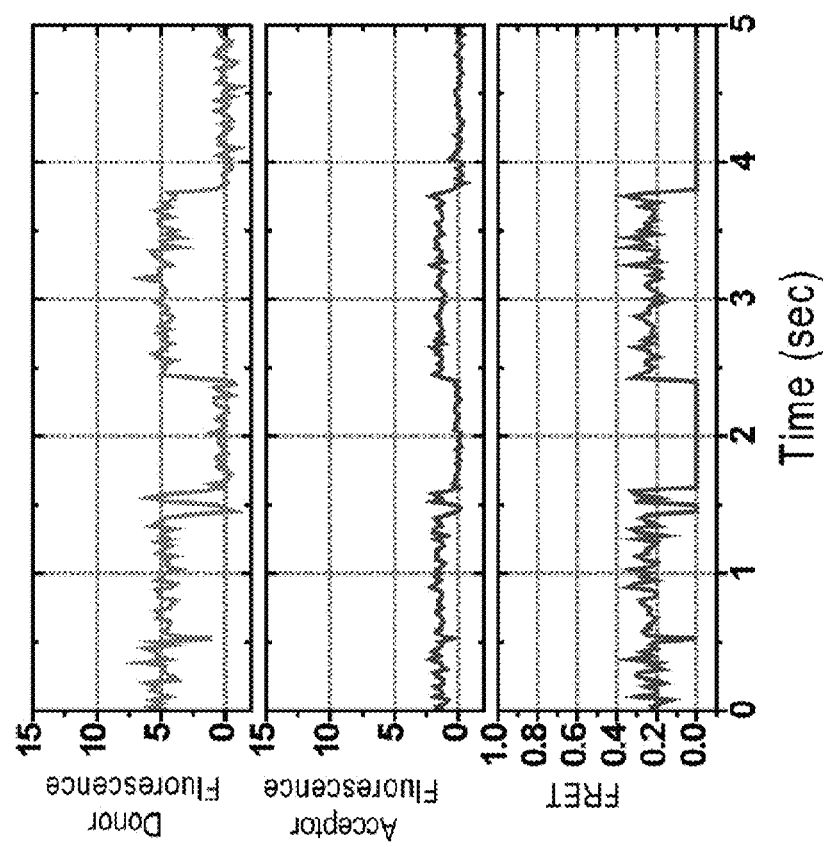
FIG. 7 illustrates a small number of fluorescent contaminants are observed in sample chambers containing imaging solutions in the absence of immobilized dye-labeled samples. An example trace shows the characteristic low apparent FRET value, low total intensity, and frequent drops in total intensity observed in such experiments.

As a test of the method's usefulness for distinguishing experimental samples from artifacts on the surface, traces were extracted from movies taken in biological buffers without experimental samples (an example trace is shown in FIG. 7). Compared to ideal experimental data, traces from this dataset had low average intensity, a lack of anti-correlated transitions in fluorescence, and frequent blinking. Combining these traces with simulated data, a dataset was created with ~34% of the traces contributed from background artifacts (much higher than typically observed). Selection with standard criteria reduced this fraction to <2%. Selection was highly specific: ~92% of the simulated traces were selected and most exclusions were the result of short acceptor dye lifetime.

Figure 4:
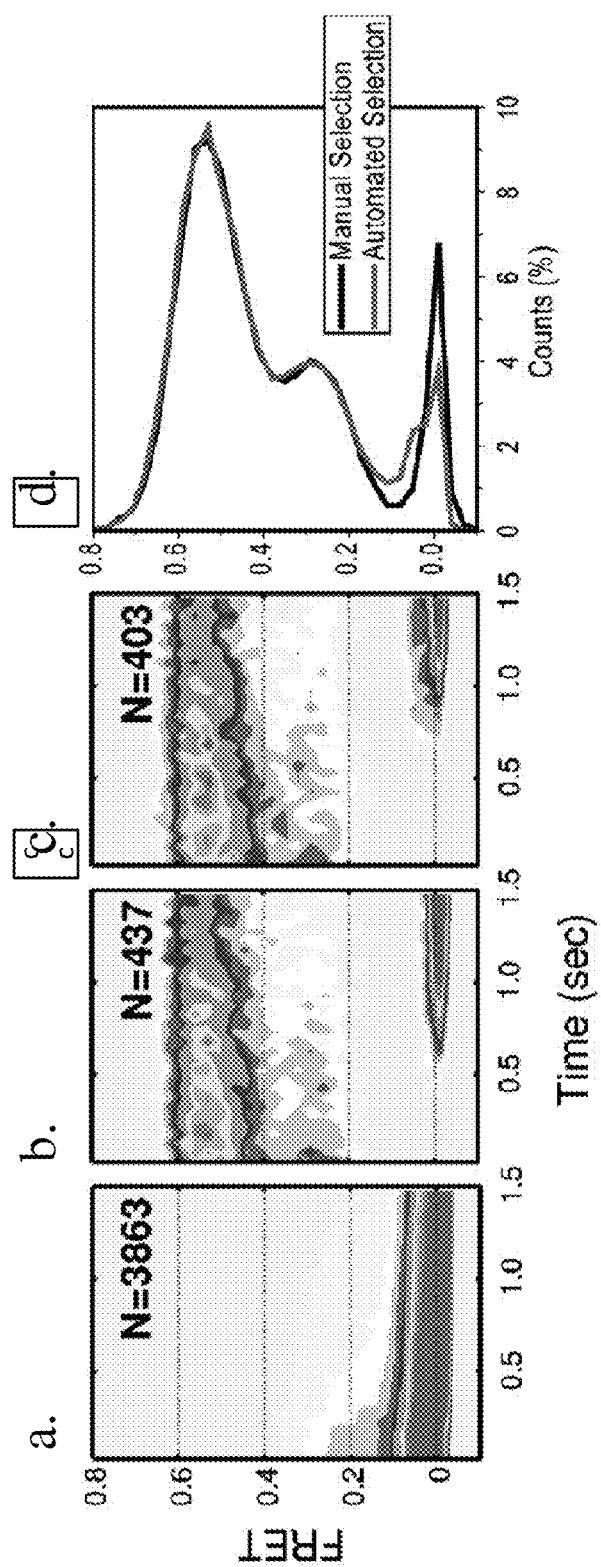
FIG. 4 illustrates trace selection using defined selection criteria in one embodiment of the present disclosure. smFRET traces from previous reports (for example, see Munro et al. 2007) were summed into a histogram and plotted as a contour plot as a function of time from the start of each imaging session. Histograms were generated from (a) all data, (b) manually selected traces, and (c) automatically selected traces, using standard criteria. (d) Time-averaged FRET histograms generated from traces selected using manual (black line) and automated methods are overlaid for comparison.

The capacity of the automated method to replace manual selection was evaluated using single-molecule fluorescence traces from published experiments, where the motions of dye-labeled tRNA molecules bound within wild-type ribosomes were measured (for example, see Munro et al. 2007). Little FRET signal is apparent in the raw data (FIG. 4a) because of the selection of background regions and ribosomes without an acceptor-labeled tRNA in the A site. Some low-FRET signal from fluorescent contaminants and other artifacts is also evident. In the published work, manual selection resulted in significant enrichment in dye-labeled ribosome particles (FIG. 4b). Selection using the automated method with standard criteria resulted in population distributions that closely resemble those produced from manually processed data (FIG. 4c-d).

Figure 5:
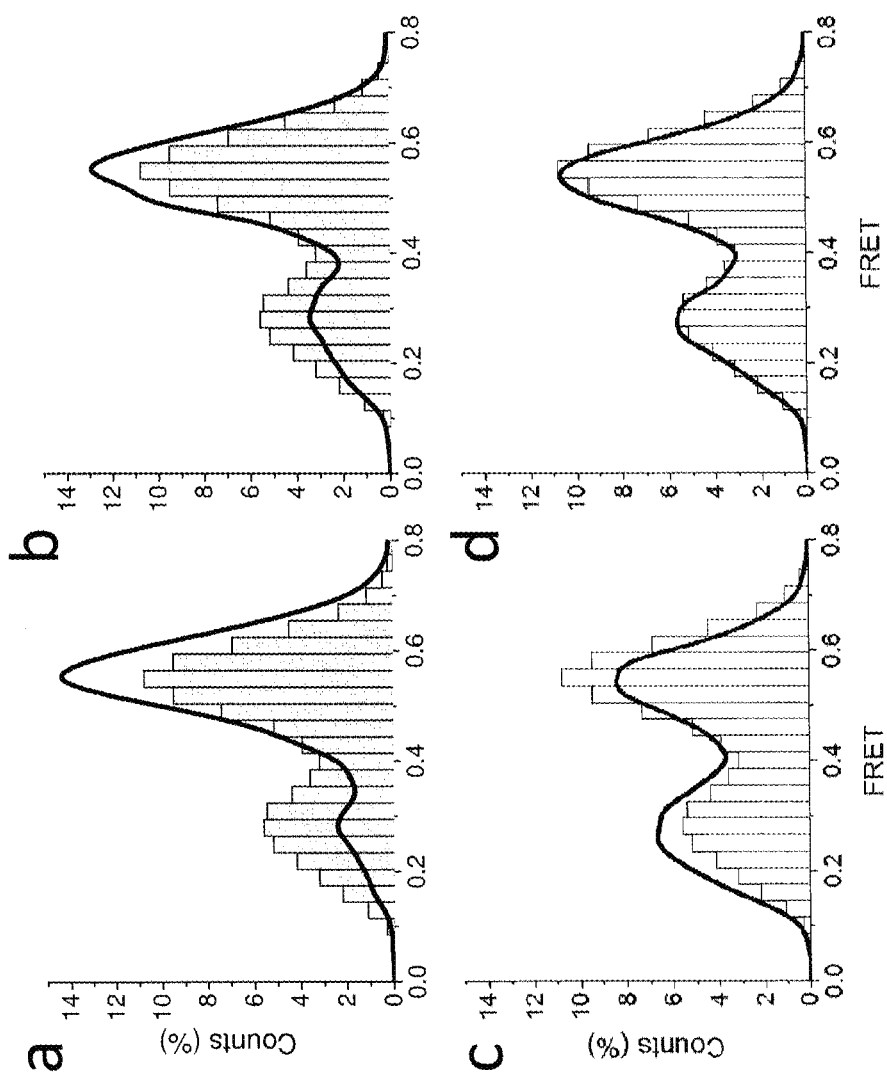
FIG. 5 illustrates evaluation of potential bias in trace selection in one embodiment of the present disclosure. (a-c) smFRET traces selected using trace-by-trace visual inspection in a previous report (Munro et al. 2007) were summed into a FRET histogram (gray bars). CC refers to correlation coefficient. (a) For comparison, FRET histograms are also shown for a subset of this data selected (black lines) by strict requirements for anticorrelation between donor and acceptor fluorescence traces: (a) $CC_{D,A}<-0.85$ or (b) $CC_{AD,AA}<-0.53$. FRET histograms are also shown for data selected by strict requirements for (c) the lifetime of the donor dye ($LT_{Donor}>300$ frames) or (d) the acceptor dye ($LT_{FRET}>140$ frames). In all cases, about one third of all traces were selected in each subset. Unbiased selection should produce a subset of data that is representative of the full population, as reflected in a lack of change in FRET histograms.

Evaluating Potential Bias in Trace Selection:

The end product of trace selection is a dataset of high quality traces useful for further analysis. With both manual and automated methods, care should be taken to ensure that the resulting subset of data is unbiased and representative of the full population. As an example, the correlation of donor and acceptor fluorescence ($CC_{D,A}$) is a key criterion used for selecting traces by visual inspection. When experimental data (manually selected traces shown in FIG. 4b) are further refined using the anti-correlation criteria, the selected subset of traces had higher average FRET values (FIG. 5a-b). This indicates that selection with this method produced a biased dataset.

When traces with long lifetimes before photobleaching are selected, no significant change in FRET state occupancies was observed (FIG. 5d). This result shows that it is possible to effectively extend observation times by selecting only traces with long lifetimes before bleaching and that this can be achieved without introducing significant bias.

The observed biasing effect provides a caution that one must ensure the selected subset is representative of the full population. Such careful control is difficult to achieve with manual selection by visual inspection. In contrast, the automated method presented here enables precise, reproducible control over selection that enables the user to minimize bias. Biasing effects may be dependent on the properties of the specific biological system under study. As shown above, however, they can be investigated using a manually pruned dataset from any system and monitoring the effect selection has on FRET histograms, state occupancies, and rate constants. In one embodiment of the present disclosure, the biasing effects of the criteria chosen by the user (or determined by an automated algorithm) may be automatically investigated given a manually pruned dataset so that the user is made aware of selection criteria that may introduce significant bias.

In some experiments the system may not be in equilibrium, for example when a component of the system is added in real time concurrent with acquisition. In this case, the system changes appreciably during acquisition. In one implementation, the appearance of FRET from a zero baseline signifies the binding of a dye-labeled molecule to the system. In one embodiment of the present disclosure, the implementation includes a method to separate out these events by detecting FRET that crosses a defined threshold in the range of 1-4 standard deviations of background noise. The event is recorded until the FRET signal drops to baseline (zero FRET) for a specified period of time (dependent on the kinetics of the system). Each of these events is extracted into distinct traces so that they can be analyzed separately. The start point of each of these traces is synchronized so that the appearance of FRET is set as time zero. In addition, the distribution of time between events (arrival time) may be quantified and displayed to the user.

Kinetic Analysis:

Given an informative labeling position, distinct states may be observed in FRET traces. In this case, one often seeks to estimate kinetic parameters that describe the dynamics. Hidden Markov Modeling (HMM) provides a statistical framework for examining the likelihood of many possible models to explain the experimental data. Here we modify a previously described method (for example, see Munro et al. 2007), where algorithms implemented for the analysis of ion channel conductance recordings are applied to FRET traces. First, a starting model with a set connectivity is optimized to fit the data using the segmental k-means (SKM) algorithm (for example, see Qin 2004). Restoration of single-channel currents using the segmental k-means method based on hidden Markov modeling (for example, see Qin 2004). Restoration of single-channel currents using the segmental k-means method based on hidden Markov modeling, (for example, see Qin 2004), resulting in an assignment of the state of the system at each point in time (an idealization). Second, the kinetic parameters in the model are iteratively adjusted to best explain the observed dwell-times from the idealization using a maximum likelihood algorithm (for example, see Qin et al. 1996, 1997).

The approach here combines the dwell-time information from all traces to find a single optimal model. This is in contrast to previous reports (for example, see McKinney et al. 2006 and Munro et al. 2007) where a model is established for each individual trace. By doing a single fitting cycle, our method is significantly faster and more accurate (for example, see Liu et al. 2010). Because fitting each trace may yield valuable information on heterogeneities in the ensemble or dispersed kinetics, such methods can be implemented as a complementary approach to the fast kinetic analysis method we disclose.

Other optimization and idealization methods may be implemented in the software platform of the present disclosure in one embodiment, and may be used for analysis, including but not exclusive to Baum-Welch (for example, see Rabiner 1989) and variational Beyes (for example, see Bronson et al. 2009). Baum-Welch (BW) is a more traditional HMM method for optimizing an initial model (for example, see Rabiner 1989 for a summary). As with SKM, Viterbi is then used for idealization using the model from BW. One advantage of both BW and variational Beyes is that they can be used to naively discover a good model by trying many possibilities and calculating scores, which facilitate the quantitative comparison of different models.

There are other approaches. One approach is thresholding, where states are assigned by binning the FRET data according to user defined limits for the possible FRET values of each state (thresholds). High-frequency noise is then filtered from the idealization. Another means of kinetic analysis from an idealization is to plot/fit exponential decays of the dwell times in each state.

There are several ways of interpreting the results from kinetic analysis methods. One method is to plot the distributions of model parameters (rates and FRET values), especially where this might reveal heterogeneity in the population, where not all samples behave identically. Another method may determine an average model that summarizes the distributions. This may be achieved by calculating the average FRET values and average rates in log space (for example, see McKinney et al. 2006 and Munro et al. 2007). This can also be achieved using transition density plots, especially where each trace samples only a fraction of the total number of FRET states (for example, see McKinney et al. 2006).

Figure 6:
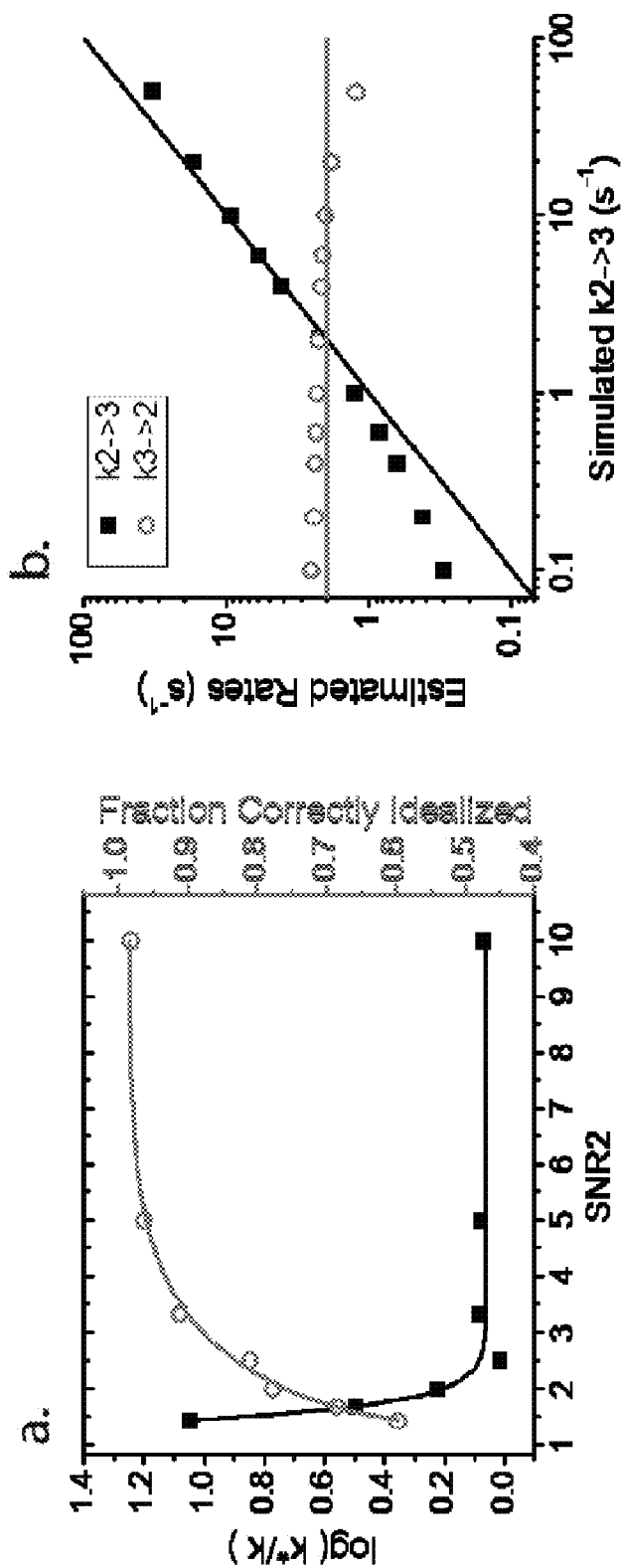
FIG. 6 illustrates kinetic analysis of simulated FRET traces in one embodiment of the present disclosure. The combination of segmental k-means idealization and maximum likelihood rate estimation yields rate estimates that are robust to experimental noise and sensitive to subtle changes. To test the method's accuracy, fluorescence and FRET traces were simulated for a two state FRET system. (a) The kinetic model was simulated with varying levels of Gaussian noise within fluorescence signals, with signal-noise ratios (SNR2) varying from 1 to 10. The accuracy of idealization is shown as the fraction of datapoints correctly assigned (open circles). The error in rate estimates is shown as the log mean of the ratio of estimated ($k_{i,j}*$) to simulated ($k_{i,j}$) rates (black squares). (b) At SNR levels comparable to experiments (SNR2=6), data were simulated where one rate was varied from 0.1 to 50 to simulate the effect of a titration of a specific perturbation. For each dataset, rates are estimated for the titrated rate (filled black squares) and the rate held constant (open gray circles). Solid lines represent the true values used to generate the simulated data.

To verify the accuracy of the proposed analysis procedure and its robustness to noise, analysis was performed on simulations of a two FRET-state system (Methods). In simulations with minimal noise (SNR2=10), >95% of the data points are correctly assigned and rate estimates are close to simulated values (FIG. 6a). Idealization and rate estimation accuracy were found to be generally robust to noise when SNR2>4.

To verify the procedure's capacity to detect subtle changes in the underlying system, simulations were performed in which one rate parameter ($k_{2\rightarrow3}$) was varied across a range of values, while the other rate parameter ($k_{3\rightarrow2}$) was held constant. Rate estimates were close to true values when $k_{2\rightarrow3}$ was between 2 and 20 sec$^{-1}$ (FIG. 6b).

The accuracy of rate estimates in experiments with slow dynamics (relative to photobleaching) is significantly improved when photobleaching rates are reduced, even when the same amount of data is used for analysis (data not shown). Where sufficient quantities of data can be obtained, such artifacts may also be reduced by selecting only long-lived traces for analysis. It may also be possible to implement corrections to existing HMM methods to improve accuracy.

EXAMPLES

The present description is further illustrated by the following examples, which should not be construed as limiting in any way. The contents of all cited references (including literature references, issued patents, published patent applications as cited throughout this application) are hereby expressly incorporated by reference.

Computer Implementation/Software:

All analysis was performed on a computer running Windows XP Professional with an Intel Core 2 Duo 2.6 GHz processor with 4 GB of RAM. An example of the analysis pipeline is implemented in MATLAB (The MathWorks), with the exception of the maximum likelihood rate estimation algorithm, which is implemented in the QuB software suite (http://www.qub.buffalo.edu). It should be understood that other computer systems, platforms, computer language, and/or programming framework may be utilized to implement the methodologies of the present disclosure.

Computer Implementation/Software: Extracting Fluorescence Traces from Movies

Fluorescence traces can be extracted from experimental wide-field movies of dye-labeled samples, for example, via a program or script such as those that can be programmed in Matlab®. FIG. 13 shows an example of a UI for software that carries out this method. This UI program, in one embodiment, loads movies acquired using MetaMorph® software or other acquisition software using the TIFF-based .STK format. Several imaging setups may be selected, including, for example, 1, 2, 3 or 4 channels (colors). With two channels, the left half of the field is assumed to be a projection of fluorescence intensity from donor fluorophores, while the right half is from acceptors. With 4 colors, the top half is assumed to have projections of the first FRET pair and bottom half is assumed to be a projection of the second FRET pair.

To open a single movie for processing, click on "Open STK." The field of view is presented as the average of the first 10 frames. With two-color imaging, donor and acceptor channels are split into separate images (left, center, respectively) and the combined donor+acceptor intensity is shown at right. Click on "Pick Peaks" to discover peaks of total (donor+acceptor) intensity. The parameter "Intensity Threshold" specifies the minimum intensity a peak must have to be considered. If this field is left blank, a threshold is automatically calculated in one embodiment of the present disclosure, e.g., using equation (1). Peaks closer than a minimal Euclidian distance are ignored, as specified under "Overlap Rejection". The integration window size may also be specified, or if left blank, automatically selected by finding a value that maximizes the calculated SNR1 of the selected traces. Each peak is represented as an unfilled circle in the field of view. Once acceptable selections have been made, click "Save Traces" to integrate the fluorescence intensity over time and save the result as a corresponding .traces file.

Often, many movies are collected in an experiment. In this case, time can be saved by clicking on the "Batch Mode" button, which will process all movies in the user-selected directory. Two checkboxes next to the "Batch Mode" button allow the user to control its operation. If "Look in subdirectories" is checked, all data will be processed, even if contained in a child folder (subfolder) in the directory selected by the user. If "Skip movies already processed" is selected, all movies that have a corresponding .traces file are ignored. A log file may be saved in the data directory whenever files are analyzed that includes the parameter settings and files processed.

Computer Implementation/Software: Selection of Traces

FIG. 14 illustrates a sample UI for evaluation of the quality and characteristics of the traces generated above. One or more input fields may be populated by the user according to the specific needs of the experiment performed and the aspects of the data the user wishes to quantify. In another embodiment, optimal values can be determined by: (1) Manual selection of an example (training) dataset; and (2) Allowing an algorithm to determine criteria that reproduce the manual selection. The new criteria can then be applied to any additional datasets after this training is completed. The user interface shown in FIG. 14 allows the user to see the distributions of trace statistics to evaluate the data and to select a specific subset of traces.

Individual or multiple traces files generated from acquired movies, e.g., as shown in FIG. 13, can be loaded by clicking an appropriate UI selection item such as a button or menu. For example, in FIG. 14, the "Open Traces File" button may be selected to load traces. Trace characteristics are calculated and their distributions are shown in a series of panels (e.g., 1402, 1404, 1406, 1408, 1410). The characteristic shown can be adjusted using the drop-down menus above each panel. A subset of the traces can be selected by choosing selection criteria in the right-hand panels (1412, 1414). In the top box (1412), standard criteria are available. In the lower box (1414), many more criteria may be selected by choosing (1) the name of the criterion (1416), (2) inequality operator (1418), and (3) a value for the criterion (1420). This interface allows new, potentially even user-defined, criteria to be added to the interface by only changing the back-end code without the need to modify the UI. Once an acceptable subset of traces has been selected the user may see a summary of the selected data by clicking "Make Contour Plot" or the traces can be saved for further use by clicking "Save Traces".

This process can be automated for a large number of datasets in one embodiment of the present disclosure, for example, by clicking on the "Batch Mode" button, which will load all traces files in a directory, select a subset using the current criteria, and save the result. This process is repeated for every sub-directory within the user-selected directory.

Computer Implementation/Software: Kinetic Analysis of Selected Traces

The traces selected for further analysis can be used to derive kinetic information. In one embodiment of the present disclosure, the user may select one of a number of algorithms available for this task, including SKM and maximum likelihood optimization (for example, see Qin et al. 1996, 1997; Qin 2004; BW, Rabiner 1989; and Variational Beyes, Bronson 2010). In general terms, these algorithms first calculate the probability of the fluorescence data given the initial model and then iteratively refine the model by choosing better parameter values and calculating the probably again until convergence. Multiple initial models may be generated having varying number of FRET states (for example from 1 to 4) and probabilities of the optimized models generated from each of these calculations can then be compared and a single best model can then be chosen. The output is an optimized kinetic model that best describes the entire set of traces or one model for each trace. An initial model may be provided by the user, but is not required, and additional parameters unique to each algorithm may be adjusted by the user. The output model may include FRET values, apparent noise levels, the number of distinct states, their kinetic connectivity, and rate constants. The results of this analysis may then be displayed to the user in several forms, such as transition density plots that show average FRET values before and after each transition between distinct states, histograms of the occupancy in each state, and kinetic constants across a set of experiments.

Computer Implementation/Software: Data Analysis Concurrent with Acquisition.

Figure 16:
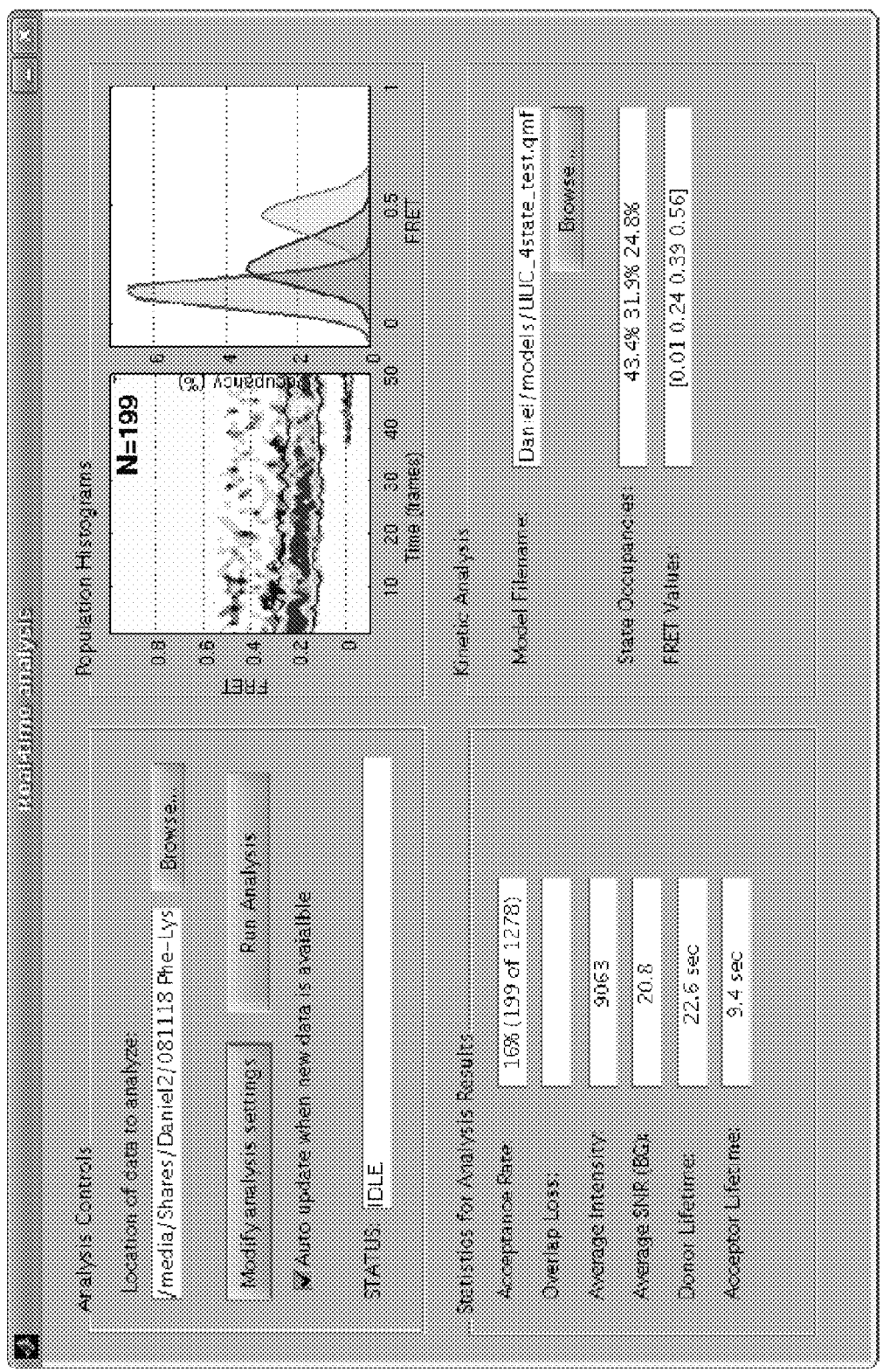
FIG. 16 illustrates UI for software that can provide data analysis concurrent with acquisition in one embodiment of the present disclosure. Once classification criteria are established and a HMM model is available, one can use the analysis pipeline to analyze data concurrent with acquisition.

The above interfaces provide a complete means of analysis of single-molecule fluorescence data, from acquired movies through kinetic analysis, in a series of distinct user interfaces. FIG. 16 illustrates a sample UI for performing the entire data analysis process within a single interface in an entirely automated manner. Trace selection criteria may first be established using preliminary data and an initial HMM model may be provided. In one embodiment of the present disclosure, the algorithm periodically checks the current directory (set by the user) for the appearance of TIFF movie files. When new files appear, the algorithm runs the algorithms responsible for extracting fluorescence traces from movies, calculation of FRET trajectories, selection of FRET traces based on defined criteria, kinetic analysis, and the display of summary statistics and figures. This enables data analysis concurrent with acquisition.

For example, referring to FIG. 16 (which may be invoked from another menu or interface, e.g., a main menu in the platform of the present disclosure, by selecting an item such as the "Real-time Analysis" button), a user may select a folder where movies have been or will be saved under "Location of data to analyze" item. To specify trace classification criteria and other settings, a user may click on "Modify analysis settings." If a HMM model is available, a user may enter a model filename (.qmf file) under "Kinetic Analysis". To analyze all data currently in the specified location, a user may click "Run Analysis". If a user wants analysis results to be updated whenever new data are acquired, the box next to "Auto update when new data is available." may be checked. Whenever a new file appears or an existing file is moved, analysis may be automatically performed and the results updated.

Figure 11:
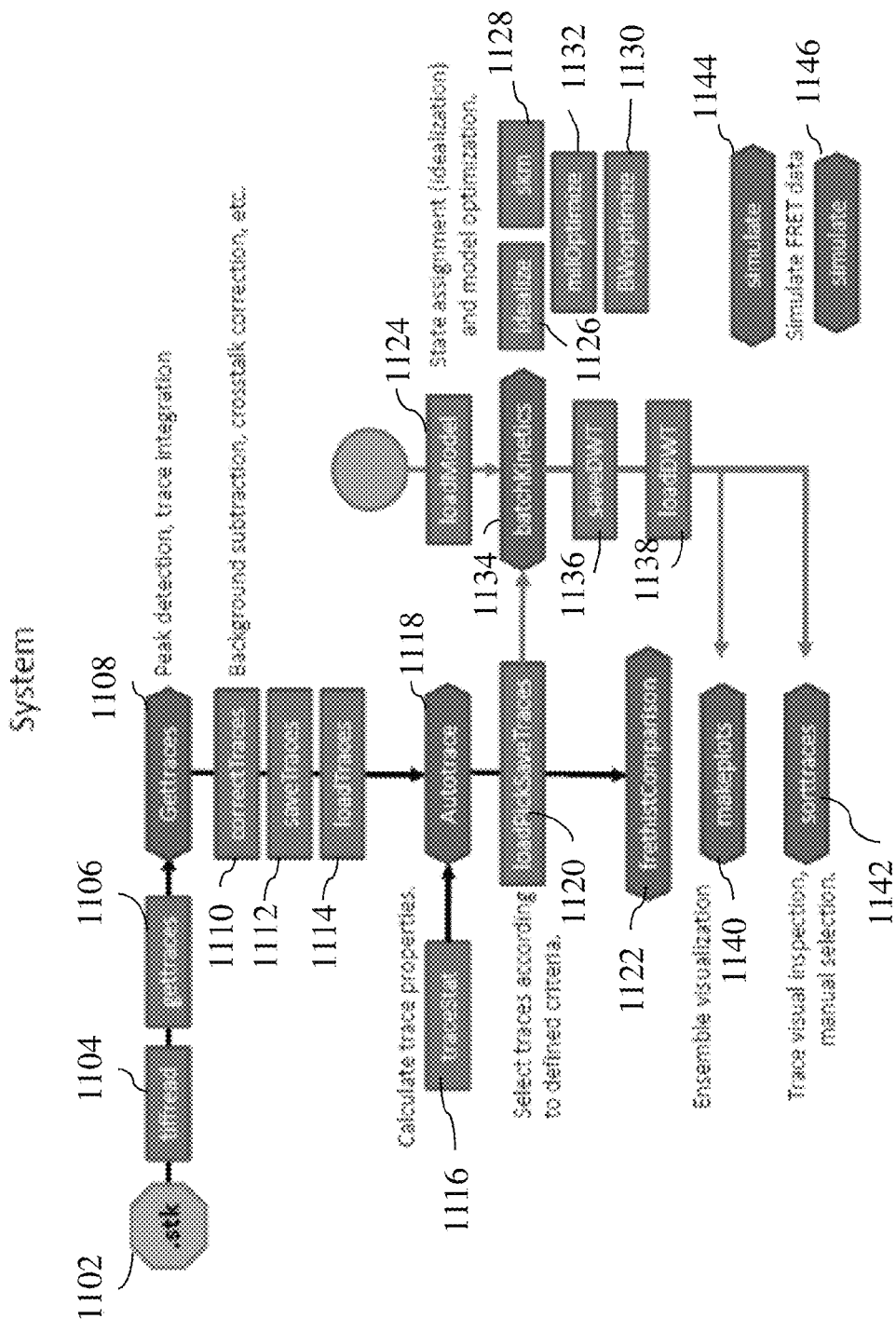
FIG. 11 illustrates overall schema for automated system in one embodiment of the present disclosure. Optimal smFRET fluorescence peaks are collected employing an integration window while removing contamination from neighboring overlapping peaks. Traces are selected with a defined set of trace statistics according to each individual experiments resulting in a refined dataset amenable to analysis.

FIG. 11 illustrates the overall schema for the automated system in one embodiment of the present disclosure. Movies of raw smFRET data may be acquired in TIFF-based .STK format 1102, which may be read at 1104. In FIG. 11, rectangular boxes refer to the code layer and the elongated hexagons refer to user interface (GUI) components. In one embodiment of the present disclosure, the underlying codes (e.g., shown by rectangular boxes) may be used independently of the GUI (hexagons), for example, in a batch mode or via interface shown in FIG. 16. At 1106 and 1108 peak detection and trace integration may be performed to acquire time traces of sources of fluorescence in the movies. At 1110, correction of the acquired time traces is performed, for instance, by subtracting background noise, performing crosstalk correction and other filtering or removing of signal contaminations. At 1112, the corrected time traces and associated metadata may be saved or stored in nonvolatile storage devices, for instance, for later retrieval. The traces may be saved in suitable data structure format for processing. At 1114, the saved traces may be loaded into memory for further processing and/or analysis. At 1116, quantitative characteristics of each trace (e.g., signal-noise ratios, lifetimes, degree of anti-correlations, number of blinking events, number of photobleaching events, highest Fret value observed in a trace, etc.) may be calculated and presented as distributions at 1118. For example, component at 1116 calculates statistics that are shown in GUI at 1118 for selecting useful traces. At 1120, traces may be selected according to defined criteria. This may be achieved with an interface such as shown in FIG. 14. For example, traces are selected with a defined set of trace statistics according to each individual experiments resulting in a refined dataset amenable to analysis. For example, FIG. 14 shows the calculated statistics and criteria (e.g., thresholds) for selecting useful smFRET traces, which criteria may have been generated automatically by the methodology of the present disclosure and which may be updated or are configurable by a user. At 1122, FRET values from the traces are summed into histograms so that multiple datasets can be compared to detect condition-induced changes. The computed histograms may be presented via a user interface, for instance.

Figure 15:
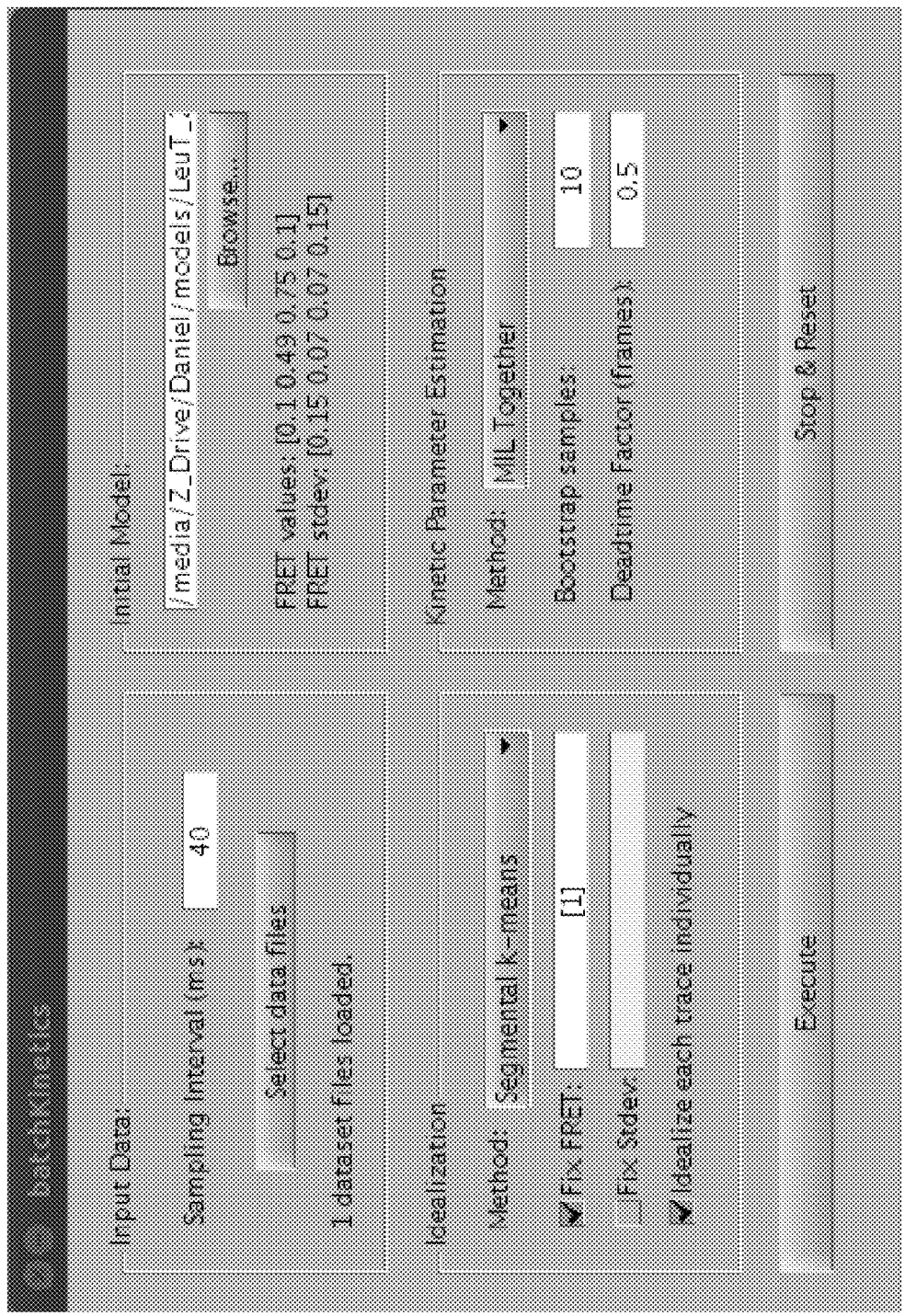
FIG. 15 illustrates a UI for software that provides an interface to kinetic analysis methods. The user can input selected traces and an initial model and an optimized model will be output along with idealization (state assignment) for all input FRET traces.

At 1124, a model may be built based on the FRET values; the model in one aspect may be used to assign states to time points in the trace (e.g., at 1126 and 1128), and kinetic parameters that explain the observed dwell-times from the assigned states in time points. For instance, optimization methodologies such as Baum-Welch (BW) 1130 (for example, see Rabiner 1989) and maximum likelihood optimization 1132 (for example, see Qin et al. 1996, 1997) may be used to optimize the model. Kinetic analysis may be performed with the user interface at 1134, enabling access to these functions (shown in FIG. 15). The analysis data may be saved at 1136, and also loaded at 1138, for instance, for visualization 1140 and/or visual inspection of traces and manual selection of traces at 1142.

Figure 12:
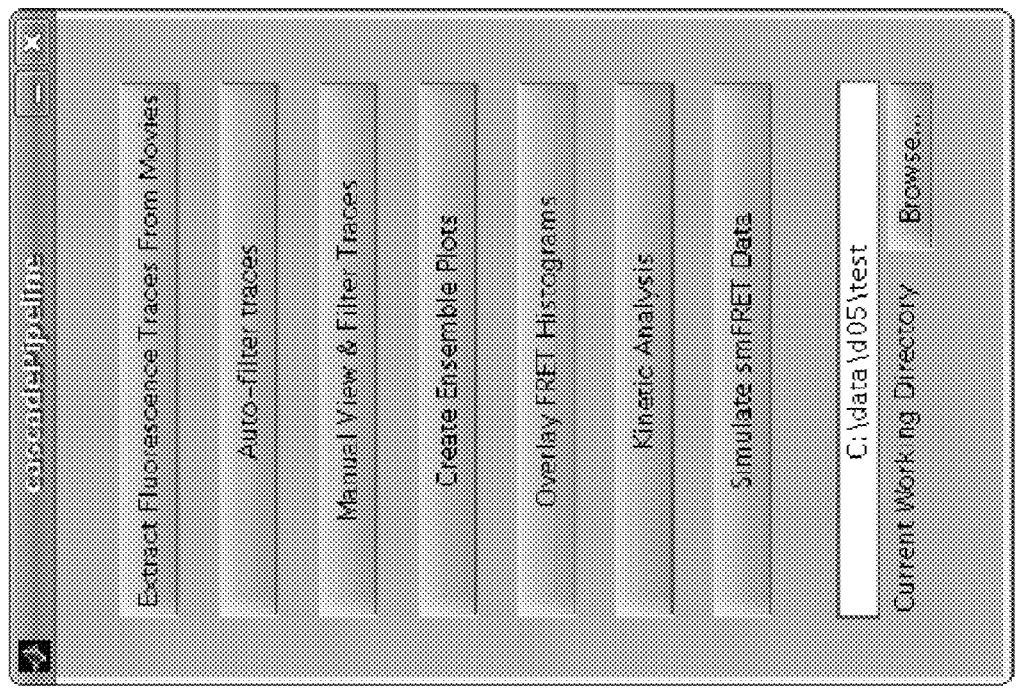
FIG. 12 illustrates an example user interface panel of software that implements the system of the present disclosure in one embodiment. The menu provides the user with access to several functions:
1. Find peaks of fluorescence corresponding to single molecules, integrate the intensity over time, and save as fluorescence traces.
2. Classify traces according to defined selection criteria and view the distributions of these selection criteria in a dataset.
3. View and manually classify traces.
4. Plot FRET-time contour plots, FRET histograms, and transition density plots from classified data.
5. Overlay FRET histograms from multiple experiments.
6. Estimate FRET and kinetic parameters using Hidden Markov Modeling tools.
7. Simulate smFRET fluorescence and FRET data from a specified model.

The routines shown at 1144 and 1146 may simulate FRET data according to a specific model, for instance from a model derived at 1134. Simulated data may be used to optimize analysis procedures. One or more routines or functions shown in FIG. 11 may be invoked by a user, for instance, by clicking on the buttons on the user interface shown in FIG. 12. The routines may be also performed automatically in a run through fashion without user having to invoke each.

As a practical consequence of automation, the above described system may then be used to quantify changes in aspects of the biological system across a range of conditions. For example, a panel of small molecule compounds may be applied to the system and any effects these compounds have on the system may be quantified immediately after acquisition of data by the analysis methods described here. Such a process would enable a user to rapidly discern which of the compounds may be a potential lead for future development as a therapeutic agent or drug.

Figure 17:
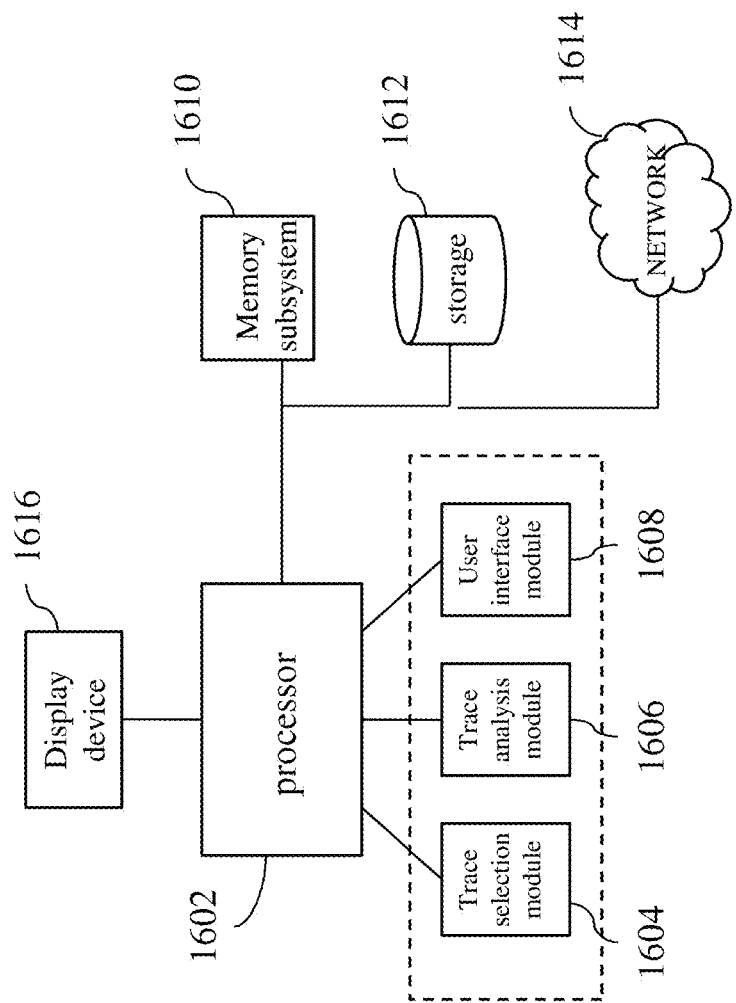
FIG. 17 is an example computer processing system that may be used to implement an automated software platform for selecting time traces and analyzing the selected time traces in smFRET experiments in one embodiment of the present disclosure.

FIG. 17 is an example computer system that may implement the automated methodologies of the present disclosure in one embodiment. The computer configuration is shown as example only; Any other computer processing configurations may be utilized, including but not limited to distributed computing, cloud computing and others. One or more processors 1602 may run one or more modules or functions that implement the methods described above. For instance, a trace time selection module or functionality 1604 may select time traces from smFRET raw image data as described herein. A time trace analysis module or functionality 1606 may execute on the processor 1602 and calculate FRET traces from the selected time traces, and further analyze the FRET traces as described herein. The computing system may also include memory subsystem 1610 as well as one or more storage devices 1612 for storing the data used and resulting from the method described herein, for example, data used in and resulting from selecting of the time traces and analysis of the FRET traces. For example, raw image intensity data may be acquired to a small-capacity, low-latency, high-throughput drive (such as a flash-memory based drive) for immediate analysis. The data may then be archived to slower, but high-capacity storage, for example, to a network file server or to computing environment such as the cloud computing environment. A user interface module or functionality 1608 may provide interfaces for interacting with a user, for instance, accepting inputs from the user such as actions to perform, various criteria and thresholds values for performing time trace selections and analysis, and presenting the results to the user, including for instance presenting the results graphically and visually. Examples of user interface screenshots are shown in FIGS. 12-15. The modules may be programming functionalities that may be programmed into an integrated circuit of a processor to execute on the processor or loaded from memory to execute on the processor. The example processing computer may also include a connection to a network 1614, via which for example, distributed computing of the methodologies of the present disclosure may be performed, and a display device 1616, for instance, which may present user interface screens such as those shown in FIGS. 12-15. It should be noted that the example computing device shown in FIG. 17 may include other devices and connections, and the present disclosure is not limited to the example configuration shown.

Example

Simulation of Single-Molecule Fluorescence Traces and Wide-Field Movies

Each trace was simulated as a sequence of continuous-time dwells in distinct FRET states drawn from single exponential distributions according to a kinetic model with two non-zero FRET states and all rates set to 2.0 sec$^{-1}$, except where specified. Initial probabilities were chosen to match steady-state occupancies in each state. Each dwell was assigned a corresponding FRET value (0, 0.29, and 0.56) and the resulting sequence was binned at 25 ms time resolution. Binning resulted in time-averaging artifacts, where FRET values are averaged when a transition occurs within a bin (for example, see Bronson et al. 2009). Ideal fluorescence traces were calculated as the fraction of total intensity emitted by the acceptor ($I_A = E_{FRET} \times I_{Total}$) and the donor ($I_D = I_{Total} - I_A$) at each time point in the ideal FRET traces. Photobleaching events, where dyes transition into permanent dark states, were simulated by drawing times from exponential distributions, with time constants of 10 and 5 seconds for donor and acceptor dyes, respectively.

Experimentally observed fluctuations in fluorescence intensity in excess of shot noise (possibly including millisecond-timescale changes in fluorophore quantum yield, dipole vector averaging, and transitions into the triplet state) were approximated by drawing intensities from a normal distribution with a mean of 437 photons and signal-noise ratio of 10. The signal-noise ratio (SNR) is the signal-noise in the limit of no shot noise or background noise and represents the theoretical limit of SNR for a particular sample.

Wide-field movies were simulated by distributing the fluorescence intensities from simulated traces (see above) over a 2D Gaussian point-spread functions ($\sigma_{PSF}=0.8$ pixels). In experiments examining fluorophore detection and trace integration (FIG. 2a-c), fluorophore positions were chosen so that all fluorophore pairs were separated by at least 4 pixels to minimize PSF overlap. In experiments examining the effects of overlapping PSFs (FIG. 2d-g), random positions were used at densities varying from 10-800 molecules per field (0.008-0.64 μm$^{-2}$). This procedure resulted in a stack of images of 64×128 pixels (1,250 μM$^2$) for donor and acceptor channels.

Shot noise was introduced by adding Gaussian noise to each individual pixel with $$SNR = \sqrt{\frac{I}{2}},$$

where I is the instantaneous fluorescence intensity of that pixel and the factor of 2 accounts for excess noise generated by electron multiplication (for example, see Robbins, M. S., and Hadwen, B. J. 2003. The Noise Performance of Electron Multiplying Charge Coupled Devices. IEEE Transactions on Electron Devices 50 (5):1227-1232 (Robbins et al. 2003)). Background noise was simulated by adding intensity from recordings of the surface in the absence of immobilized fluorophores. All simulation parameters were chosen to closely approximate experimental observations of surface-immobilized E. coli ribosomes containing Cy3-labeled s$^4$U-tRNA$^{fMet}$ in the P-site and Cy5-labeled acp$^3$-tRNA$^{Phe}$ in the A-site under standard illumination conditions.

Single Molecule Detection and Extraction of Fluorescence Traces from Wide-Field Movies:

For each acquired movie, a composite image of donor and acceptor intensity projections was generated by averaging the first 10 frames of a wide-field movie (for example, see Roy et al. 2008). Surface-localized fluorophore pairs were located as pixels with intensity greater than their four nearest neighbors and greater than a defined threshold above background intensity. The intensity threshold was calculated according to equation 1, where N$_{threshold}=8$ and I$_{BG}$ is the intensity from the last 10 frames of the movie in regions not covered by the PSF of picked peaks of intensity, and with intensity in the lowest quartile of intensity. Fluorophore pairs detected near the edges of the image (3 pixels) were ignored because of optical artifacts in these locations. Fluorophore pairs closer than 2.5 pixels were also removed to avoid PSF overlap, except where specified.

To generate fluorescence traces from each detected fluorophore pair, intensity is summed over a set of N$_{sum}$ pixels in the 3×3 pixel region proximal to each PSF. The average background intensity observed after photobleaching was then subtracted from each donor and acceptor trace. Donor to acceptor channel intensity bleed-through (for example, see Roy et al. 2008) was corrected according to the equation:

$I_A = I_A - \beta \times I_D$, where $I_A$ and $I_D$ are the acceptor and donor fluorescence intensities, respectively, and $\beta=0.075$ was measured experimentally (for example, see Munro et al. 2007). FRET traces were then calculated according to the equation: $E=I_A/(I_A+I_D)$. FRET is set to zero in intervals where total intensity $(I_A+I_D)$ is below the intensity threshold; FRET is not defined due to the lack of fluorescence information.

smFRET Trace Classification:

The sharp drops in total fluorescence intensity that occur upon photobleaching were used to count the number of such events in each trace. Median-filtered (N=9 frames) total fluorescence $(I_D+I_A)$ signals were examined for drops in intensity with a magnitude $>3 \times \sigma_{BG}$, where the signal intensity never returned its previous average level. The algorithm correctly assigned the time of the single-step photobleaching event within 2 frames in all traces from simulations with $<SNR1>=20$.

For the analysis of experimental smFRET data, traces were selected only if they passed the following criteria: $N_{blink}<3$, $SNR1>8$, $CC_{D,A}<0.5$, $LT_{FRET}>15$ frames, $E_{max}>0.3$, and exactly one photobleaching event. For the estimation of kinetic parameters, the more stringent criteria $LT_{FRET}>40$ frames (1 sec.) was applied.

Kinetic Analysis of FRET Traces:

To establish FRET values, an initial model was defined with 3 FRET states with FRET values and standard deviations derived from histogram fitting and all possible rate constants in the fully-connected model set to 1.0 sec$^{-1}$. Initial probabilities of non-zero FRET states were set equal. FRET traces were truncated to the last data point with FRET above background levels (E>0.13). FRET traces were idealized using the segmental k-means algorithm (for example, see Qin 2004) implemented in MATLAB and all model parameters were allowed to vary. The maximum likelihood rate estimation algorithm (for example, see Qin et al. 1996, 1997) was then used to optimize a single kinetic model that best explains all of the idealizations.

Figure 9:
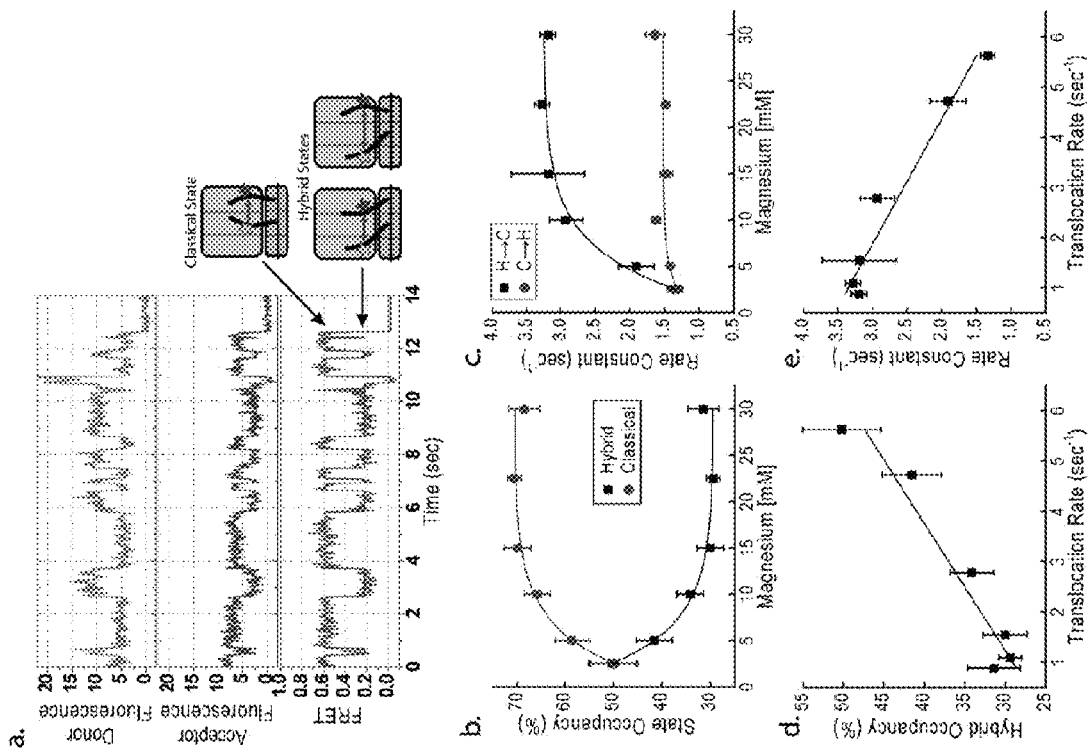
FIG. 9 illustrates experimental validation of the automated analysis pipeline in one embodiment of the present disclosure.

FIG. 9 illustrates experimental validation of the automated analysis pipeline in one embodiment of the present disclosure. smFRET imaging experiments were performed on surface immobilized wild-type ribosome complexes containing Cy3-labeled, deacylated tRNA-fMet in the P site and Cy5-labeled fMet-Phe-tRNA$^{Phe}$ in the A site (Methods). (a) Example single-molecule fluorescence (Cy3 in green, Cy5 in red; top panel) and FRET (blue; lower panel) traces are shown, with the idealization (solid line overlaid on the FRET trace) showing two distinct non-zero FRET states: high FRET reflects a Classical configuration and lower FRET reflects Hybrid state translocation intermediates. Imaging experiments were performed in buffer containing variable levels of magnesium. Under each condition, (b) time-averaged state occupancies and (c) rate constants were quantified using segmental k-means and maximum likelihood rate estimation algorithms (Methods). Error bars show standard error of experiments from three separate days. Pre-steady-state measurements of the rate of single-step mRNA:tRNA translocation through the ribosome were performed under similar conditions to smFRET experiments (Methods). (d) Hybrid state occupancy and (e) the rate out of Hybrid ($k_{H \to C}$) are shown versus translocation rates (black squares), with lines showing linear correlation (Pearson correlation coefficient>0.98, p<0.01).

Figure 10:
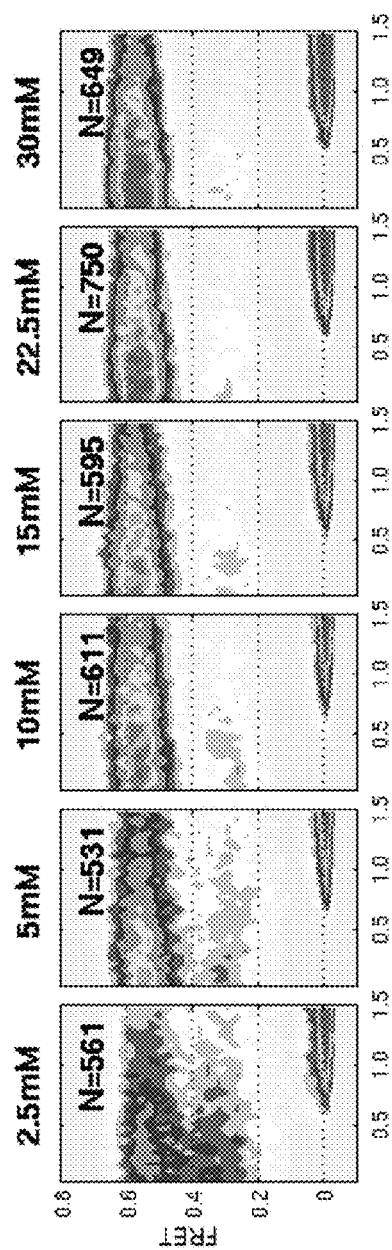
FIG. 10 illustrates smFRET traces from experiments performed at specific $Mg^{2+}$ concentrations, where traces from individual molecules were summed into histograms to reveal the population behavior under each buffer condition.

FIG. 10 illustrates smFRET traces from experiments performed at specific Mg$^{2+}$ concentrations, where traces from individual molecules were summed into histograms to reveal the population behavior under each buffer condition. FRET values near zero arise from blinking and photobleaching. At elevated Mg$^{2+}$ concentrations, an increase in occupancy in high FRET values is observed in a monotonic, concentration-dependant fashion. Time averaged histograms from each condition are shown at right for comparison.

The methodologies of the present disclosure need not be limited to experiments of single molecules. Rather, the methodologies and/or computer-implemented platform of the present disclosure may be also applied in bulk experiments.

Various aspects of the present disclosure may be embodied as a program, software, or computer instructions stored in a computer or machine usable or readable storage medium, which causes the computer or machine to perform the steps of the method when executed on the computer, processor, and/or machine. A computer readable storage medium or device may include any tangible device that can store a computer code or instruction that can be read and executed by a computer or a machine. Examples of computer readable storage medium or device may include, but are not limited to, hard disk, diskette, memory devices such as random access memory (RAM), read-only memory (ROM), optical storage device, and other recording or storage media.

The system and method of the present disclosure may be implemented and run on a general-purpose computer or special-purpose computer system. The computer system may be any type of known or will be known systems and may typically include a processor, memory device, a storage device, input/output devices, internal buses, and/or a communications interface for communicating with other computer systems in conjunction with communication hardware and software, etc. While the above description explained the automated methodologies with reference to software, it should be understood that the methodologies of the present disclosure may be also programmed into a specialized processor or integrated circuit.

The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, server. A module may be a component of a device, software, program, or system that implements some "functionality", which can be embodied as software, hardware, firmware, electronic circuitry, or others.

As used in the present disclosure, the singular forms "a", "an" and "the" are intended to include the plural forms as well, unless the context clearly indicates otherwise.

The components of the flowcharts and block diagrams illustrated in the figures may show various embodiments of the present invention. It is noted that the functions and components need not occur in the exact order shown in the figures. Rather, unless indicated otherwise, they may occur in different order, substantially simultaneously or simultaneously. Further, one or more components or steps shown in the figures may be implemented by special purpose hardware, software or computer system or combinations thereof.

The embodiments described above are illustrative examples and it should not be construed that the present invention is limited to these particular embodiments. Thus, various changes and modifications may be effected by one skilled in the art without departing from the spirit or scope of the invention as defined in the appended claims.

We claim:

1. A computer-implemented method to automatically select time traces from a fluorescence experiment, comprising:
   capturing results of the fluorescence experiment in a moving image;
   localizing sources of fluorescence in the moving image, wherein locations of sources of fluorescence are determined by finding intensity maxima within an integration window that cross a defined threshold which is computed based on background noise in the moving image and signal intensities of said sources;
   producing time traces of each fluorescent source by monitoring fluorescence intensity of said localized sources in the moving image over time;
   removing unuseful time traces from said produced time traces; and
   selecting useful time traces from said produced time traces based on one or more defined criteria,
   wherein the steps of capturing, localizing, producing, removing and selecting are performed by a processor.

2. The method of claim 1, wherein a time trace is identified as being unuseful if a point-spread function of its source of fluorescence overlaps with a point-spread function of the source of fluorescence of another time trace.

3. The method of claim 2, wherein a time trace is identified as being unuseful if its centroid is closer in pixel distance to a centroid of another time trace than a proximity threshold.

4. The method of claim 2, wherein a time trace is identified as being unuseful if its average total intensity is more than two standard deviations from the mean.

5. The method of claim 2, wherein a time trace is identified as being unuseful if, after median filtering a total fluorescence signal of the time trace, drops in signal intensity larger than a threshold value are detected that do not return to previous levels.

6. The method of claim 1, wherein useful time traces are identified based on selected signal-noise ratios (SNR), FRET Lifetime, degree of anti-correlation, number of blinking events, or highest FRET value observed in a trace, or combinations thereof.

7. An automated system for analysis of data from fluorescence experiments, comprising:
   a processor comprising hardware configured to:
   capture results of the fluorescence experiments in a moving image, localize sources of fluorescence in the moving image produce time traces of each fluorescent source by monitoring fluorescence intensity of said localized sources in the moving image over time, remove unuseful time traces from said produced time traces, select useful time traces from said produced time traces based on one or more defined criteria
   calculate FRET traces from said useful time traces, and analyze said FRET traces,
   wherein a time trace is identified as being unuseful if a point-spread function of its source of fluorescence overlaps with a point-spread function of the source of fluorescence of another time trace.

8. The system of claim 7, wherein the processor comprising hardware is further configured to display a user interface to interactively present statistical characteristics of said time traces, receive one or more user input for selecting said useful time traces and analyzing said FRET traces, and present analysis results of said FRET traces.

9. The system of claim 8, the processor comprising hardware is further configured to store said useful time traces and said analysis results of said FRET traces in a storage device.

10. The system of claim 7, wherein locations of sources of fluorescence are determined by finding intensity maxima within an integration window that cross a defined threshold.

11. The system of claim 10, wherein the defined threshold is computed based on background noise in the moving image and signal intensities of said sources.

12. The system of claim 7, wherein a time trace is identified as being unuseful if its centroid is closer in pixel distance to a centroid of another time trace than a proximity threshold.

13. The system of claim 7, wherein a time trace is identified as being unuseful if its average total intensity is more than two standard deviations from the mean.

14. The system of claim 7, wherein a time trace is identified as being unuseful if, after median filtering a total fluorescence signal of the time trace, drops in signal intensity larger than a threshold value are detected that do not return to previous levels.

15. The system of claim 7, wherein useful time traces are identified based on selected signal-noise ratios (SNR), FRET Lifetime, degree of anti-correlation, number of blinking events, or highest FRET value observed in a trace, or combinations thereof.

16. A non-transitory computer readable storage medium storing a program of instructions executable by a machine to perform a method to automatically select time traces from a fluorescence experiment, comprising:
   capturing results of the fluorescence experiment in a moving image;
   localizing sources of fluorescence in the moving image;
   producing time traces of each fluorescent source by monitoring fluorescence intensity of said localized sources in the moving image over time;
   removing unuseful time traces from said produced time traces; and
   selecting useful time traces from said produced time traces based on one or more defined criteria,
   wherein the defined criteria is computed based on background noise in the moving image and signal intensities of said sources.

17. The non-transitory computer readable storage medium of claim 16, wherein locations of sources of fluorescence are determined by finding intensity maxima within an integration window that cross a defined threshold.

18. The non-transitory computer readable storage medium of claim 16, wherein a time trace is identified as being unuseful if a point-spread function of its source of fluorescence overlaps with a point-spread function of the source of fluorescence of another time trace.

19. The non-transitory computer readable storage medium of claim 18, wherein a time trace is identified as being unuseful if its centroid is closer in pixel distance to a centroid of another time trace than a proximity threshold.

20. The non-transitory computer readable storage medium of claim 18, wherein a time trace is identified as being unuseful if its average total intensity is more than two standard deviations from the mean.

21. The non-transitory computer readable storage medium of claim 18, wherein a time trace is identified as being unuseful if, after median filtering a total fluorescence signal of the time trace, drops in signal intensity larger than a threshold value are detected that do not return to previous levels.

22. The non-transitory computer readable storage medium of claim 16, wherein useful time traces are identified based on selected signal-noise ratios (SNR), FRET Lifetime, degree of anti-correlation, number of blinking events, or highest FRET value observed in a trace, or combinations thereof.

23. The non-transitory computer readable storage medium of claim 22, wherein one or more of said signal-noise ratios (SNR), FRET Lifetime, degree of anti-correlation, number of blinking events, or highest FRET value observed in a trace are computed automatically from said produced time traces.

24. The non-transitory computer readable storage medium of claim of 16, wherein the fluorescence experiment includes a single-molecule fluorescence experiment.

25. The method of claim 1, wherein the fluorescence experiment includes a single-molecule fluorescence experiment.

26. The system of claim 7, wherein the fluorescence experiment includes a single-molecule fluorescence experiment.

27. The method of claim 1, wherein the selected time traces are analyzed by calculating FRET traces from the selected traces by a processor and analyzing said FRET traces by the processor.

28. The method of claim 27, wherein analysis of said FRET traces utilizes hidden Markov modeling.

29. The method of claim 27, wherein the dwell-time information from multiple selected time traces is used to find at least one optimal model.

30. The method of claim 29, wherein the dwell-time information from all time traces are used to find a single optimal model.

31. The method of claim 27, wherein the analysis of said FRET traces assigns system states to time points in the time traces.

32. The method of claim 31, wherein a segmental k-means (SKM) algorithm is used to assign said system state.

33. The method of claim 27, wherein the analysis of said FRET traces estimates kinetic parameters of a system.

34. The method of claim 33, wherein a maximum likelihood algorithm is used to estimate said kinetic parameters.

* * * * *